United States Patent [19]
de Boer et al.

[11] Patent Number: 5,747,034
[45] Date of Patent: May 5, 1998

[54] METHODS AND MATERIALS FOR THE INDUCTION OF T CELL ANERGY

[75] Inventors: Mark de Boer, Beverwijk, Netherlands; Leah B. Conroy, Pacifica, Calif.

[73] Assignee: Chiron Corporation, Emeryville, Calif.

[21] Appl. No.: 200,716

[22] Filed: Feb. 18, 1994

Related U.S. Application Data

[63] Continuation-in-part of Ser. No. 15,147, Feb. 9, 1993, which is a continuation-in-part of Ser. No. 910,222, Jul. 9, 1992, Pat. No. 5,397,703.

[51] Int. Cl.$^6$ .......................... A61K 39/395; C12N 5/12; C12P 21/08; C07K 16/18
[52] U.S. Cl. .................... 424/137.1; 424/141.1; 424/156.1; 435/70.21; 435/172.2; 435/240.27; 530/388.1; 530/387.5; 530/387.1; 530/388.85; 530/809; 530/387.3
[58] Field of Search ........................ 424/153.1, 154.1, 424/158.1, 137.1, 141.1, 156.1; 530/388.23, 388.25, 388.73, 388.75, 388.1, 387.5, 387.1, 388.85, 387.3, 809; 435/240.27, 70.21, 172.2

[56] References Cited

U.S. PATENT DOCUMENTS

| | | |
|---|---|---|
| 4,683,195 | 7/1987 | Mullis et al. |
| 4,683,202 | 7/1987 | Mullis |
| 4,689,299 | 8/1987 | Insel et al. |
| 4,886,796 | 12/1989 | Eichner et al. |
| 4,923,872 | 5/1990 | Kostlan et al. |
| 5,068,223 | 11/1991 | Lipsky et al. |
| 5,100,899 | 3/1992 | Calne |

FOREIGN PATENT DOCUMENTS

| | | |
|---|---|---|
| 92/00092 | 1/1992 | WIPO |
| 92/15671 | 9/1992 | WIPO |
| 93/00431 | 1/1993 | WIPO |

OTHER PUBLICATIONS

Cosimi, et al., "Use of Monoclonal LAntibodies To T–Cell Subsets for Immunologic Monitoring and Treatment in Recipients of Renal Allografats," The New England Journal of Medicine, 305:308–313 (Aug. 6, 19881).
Kriegler, et al., "A Novel Form of TNF/Cachectin Is a Cell Surface Cytotoxic Transmembrane Protein: Ramifications for the Complex Physiology of TNF," Cell 53:45–53 (1988).
Co, M.S. et al., Nature, 351:501–502, 6 Jun. 1991.
Brostoff, J. et al., edit. Clinical Immunology, pub. Gower Medical, pp. 27.8 and 28.4–28.5, 1991.
Waldmann, T.A., Science, 252:1657–1662, Jun. 1991.
Harris, W.J. et al., TIBTECH, 11:42–44, Feb. 1993.
Winter, G. et al., TIPS, 14:139–143, May 1993.
Freeman, G.J. et al., Science, 262:909–911, Nov. 5, 1993.
Clark and Shu, "Association Between IL–6 and CD40 Signaling IL–6 Induces Phosphorylation of CD40 Receptors", J. Immunol, 145(5):1400–1406 (Sep. 1, 1990).

Sato et al., "Biological Effects in Vitro of Monoclonal Antibodies to Human Epidermal Growth Factor Receptors", Mol. Biol. Med., 1:511–529 (1983).
Aruffo and Seed, "Molecular cloning of a CD28 cDNA by high–efficiency COS cell expression system," Proc. Natl. Acad. Sci. (USA), 84:8573–8577 (Dec. 1987).
Aruffo et al., "The Lymphocyte Glycoprotein CD6 Contains a Repeated Domain Structure Characteristic of a New Family of Cell Surface and Secreted Proteins," J. Exp. Med., 174:949–952 (Oct. 1991).
Barneveld et al., "Monoclonal Antibodies against Human β–Glucocerebrosidase," Eur. J. Biochem., 134:585–589 (1983).
Boussiotis et al., "Activated human B lymphocyte express three CTLA–4 counterreceptors that contimulate T–cell activation," Proc. Natl. Acad. Sci. (USA), 90:11059–11063 (Dec. 1993).
Cafiso et al., "Preparation of Unilamellar Lipid Vesicles at 37° C. by Vaporization Methods," Biochem. Biophys. Acta, 649:129–132 (1981).
de Boer et al., "Functional characterization of a novel anti–B7 monoclonal antibody," Eur. J. Immunol, 22:3071–3075 (1992).
de Boer et al., "Generation of monoclonal antibodies to human lymphocyte cell surface antigens using insect cells expressing recombinant proteins," J. Immunol. Methods, 152:15–23 (1992).
Dharakul et al., "Immunization with Baculovirus–Expressed Recombinant Rotavirus Proteins VP1, VP4, VP6, and VP7 Induces CD8$^+$T Lymphocytes that Mediate Clearance of Chronic Rotavirus Infection in SCID Mice," J. Virol., 65(11):5928–5932 (Nov. 1991).
DiSanto et al., "Generation of anti–human CD8β–specific antibodies using transfectants expressing mixed–species CD8 heterodimers," J. Immunol. Methods, 141:123–131 (1991).
Fleming et al., "In Situ Expression of a B7–Like Adhesion Molecule on Keratinocytes from Human Epidermis," J. Investigative Dermatology, 101(5):754–758 (Nov. 1993).
Fraser et al., "Regulation of Interleukin–2 Gene Enhancer Activity by the T Cell Accessory Molecule CD28," Science, 251:313–316 (Jan. 18, 1991).
Freedman et al., "B7, A B Cell–Restricted Antigen that Identifies Preactivated B Cells," J. Immunol., 139(10):3260–3267 (Nov. 15, 1987).

(List continued on next page.)

Primary Examiner—Susan A. Loring
Attorney, Agent, or Firm—Donald J. Pochopien; Paul B. Savereide; Robert P. Blackburn

[57] ABSTRACT

Anti-B7-1 antibodies or other B7-1 ligands may be used to prevent or treat a T-cell-mediated immune system disease in a patient or to induce antigen-specific tolerance.

The anti-B7-1 antibodies may be used to cause T cell anergy, treat allograft transplant rejection, treat graft versus host disease, and prevent or treat rheumatoid arthritis. An immunosuppressive agent is co-administered with the antibody.

17 Claims, 13 Drawing Sheets

OTHER PUBLICATIONS

Freeman et al., "B7, A New Member of the Ig Superfamily with Unique Expression on Activated and Neoplastic B Cells," *J. Immunol*, 143(8):2714–2722 (Oct. 15, 1989).

Freedman et al., "Selective Induction of B7/BB–1 on Interferon–γ Stimulated Monocytes," *Cell. Immunol.*, 137:429–437 (1991).

Gabizon et al., "Liposomes as In Vivo Carriers of Adriamycin: Reduced Cardiac Uptake and Preserved Antitumor Activity in Mice," *Cancer Research*, 42:4734–4739 (Nov. 1982).

Go et al., "Anergized T Cell Clones Retain Their Cytolytic Ability," *J. Immunol*, 150(2):367–376 (Jan. 15, 1993).

Golub, Immunology A Synthesis, pp. 19–20, Sinauer Associates, Inc. (1987).

Haffar et al., "Costimulation of T–Cell activation and virus production by B7 antigen on activated $CD4^+$ T cells from human immunodeficiency virus type 1–infected donors," *Proc. Natl. Acad. Sci. USA*, 90:11094–11098 (Dec. 1993).

Harding et al., "CD28–mediated signaling co–stimulates murine T cells and prevents induction of anergy in T–cell clones," *Nature*, 356:607609 (Apr. 16, 1992).

Harper et al., "CTLA–4 and CD28 Activated Lymphocyte Molecules are Closely Related in Both Mouse and Human as to Sequence, Message Expression, Gene Structure, and Chromosomal Location," *J. Immunol*, 147(3):1037–1044 (Aug. 1, 1991).

Gimmi et al., "B–cell surface antigen B7 provides a costimulatory signal that induces T cells to proliferate and secrete interleukin 2," *Proc. Natl. Acad. Sci.* (USA) 88:6575 (1991).

Hathcock et al., "Identification of an Alternative CTLA–4 Ligand Costimulatory for T Cell Activation," *Science*, 262:905–911 (Nov. 5, 1993).

Hawrylowicz and Unanue, "Regulation of Antigen–Presentation–I," *J. Immunol.*, 141(12):4083–4088 (Dec. 15, 1988).

Jenkins and Schwartz, "Antigen Presentation by Chemically Modified Splenocytes Induces Antigen–Specific T Cell Unresponsiveness in Vitro and in Vivo," *J. Exp. Med.*, 165:302–319 (Feb. 1987).

Jenkins et al., "Allogeneic Non–T Spleen Cells Restore the Responsiveness of Normal T Cell Clones Stimulated with Antigen and Chemically Modified Antigen–Presenting Cells," *J. Immunol.*, 140(10):3324–3330 (May 15, 1988).

Jenkins et al., "Molecular events in the induction of a nonresponsive state in interleukin 2–producing helper T–lymphocyte clones," *Proc. Natl. Acad. Sci.* (USA), 84:5409–5413 (Aug. 1987).

June et al., "Evidence for the Involvement of Three Distinct Signals in the Induction of IL–2 Gene Expression in Human T Lymphocytes," *J. Immunol.*, 143(1):153–161 (Jul. 1, 1989).

June et al., "Role of the CD28 receptor in T–cell activation," *Innun. Today*, 11(6):211–216 (1990).

June et al., "T–Cell Proliferation Involving the CD28 Pathway is Associated with Cyclosporine–Resistant Interleukin 2 Gene Expression," *Mol. Cell. Biol.*, 7(12):4472–4481 (Dec. 1987).

Knauf et al., Relationship of Effective Molecular Size to Systemic Clearance in Rats of Recombinant Interleukin–2 Chemically Modified with Water–soluble Polymers, *J. Bio. Chem.*, 263(29):15064–15070 (Oct. 15, 1988).

Kohler and Milstein, "Continuous cultures of fused cells secreting antibody of predefined specificity," *Nature*, 256:495–496 (Aug. 7, 1975).

Kosco–Vilbois et al., "Follicular Dendritic Cells Help Resting B Cells to Become Effective Antigen–presenting Cells: Induction of B7/BB1 and Upregulation of Major Histocompatibility Complex Class II Molecules," *J. Exp. Med.*, 178:2055–2066 (Dec. 1993).

Kubota et al., "Identification and Gene Cloning of a New Phosphatidylinositol–Linked Antigen Expressed on Mature Lymphocytes," *J. Immunol.*, 145(11):3924–3931 (Dec. 1, 1990).

Lenschow et al., "Expression and functional significance of an additional ligand for CTLA–4," *Proc. Natl. Acad. Sci USA*, 90:11054–11058 (1993).

Lenschow et al., "Long–Term Survival of Xenogeneic Pancreatic Islet Grafts Induced by CTLA4Ig," *Science*, 257:789–792 (Aug. 7, 1992).

Lin et al., "Long–Term Acceptance of Major Histocompatibility Complex Mismatched Cardiac Allografts Induced by CTLA4Ig Plus Donor–specific Transfusion," *J. Exp. Med.*, 178:1801–1086 (Nov. 1983).

Linsley et al., "CTLA–4 is a Second Receptor for the B Cell Activation Antigen B7," *J. Exp. Med.*, 174:561–569 (Sep. 1991).

Linsley et al., "Immunosuppression in Vivo by a Soluble Form of the CTLA–4 T Cell Activation Molecule," *Science*, 257,792–795 (Aug. 7, 1992).

Mueller et al., "Clonal Expansion Versus Functional Clonal Inactivation: A Costimulatory Signalling Pathway Determines the Outcome of T Cell Antigen Receptor Occupancy," *Ann Rev. Immunol.*, 7:445–480 (1989).

Otten et al., "Split Anergy in a CD8+ Cell Receptor–Dependant Cytolysis in the Absence of Interleukin–2 Production," *Science*, 251:1228–1231 (Mar. 8, 1991).

Poznansky, "Biological Approaches to the Controlled Delivery of Drugs: A Critical Review," *Pharm. Revs.*, 36(4), 277 (1984).

Ra et al., "A macrophage Fcγ receptor and the mast cell receptor for IgE share an identical subunit," *Nature*, 341:752–754 (Oct. 26, 1989).

Razi–Wolf et al., "Evidence for an additional ligand, distinct from B7, for the CTLA–4 receptor," *Proc. Natl. Acad. Sci.* (USA), 90:11182–11186 (Dec. 1993).

Schwartz, "A Cell Culture Model for T Lymphocyte Clonal Anergy," *Science*, 248:1349–1356 (Jun. 15, 1990).

Schwartz, "Costimulation of T Lymphocytes: The Role of CD28, Ctla–4, and B7/BB1 in Interleukin–2 Production and Immunotherapy," *Cell*, 71:1065–1068 (Dec. 24, 1992).

Sekine et al., "Expression of human papillomavirus type 6b E2 gene product with DNA–binding activity in insect (*Bombyx mori*) cells using a baculovirus expression vector," *Gene*, 65:187–193 (1988).

Selvakumar et al., "Genomic organization and chromosomal location of the human gene encoding the B–lymphocyte activation antigen B7," *Immunogenet.*, 36:175–181 (1992).

Smith et al., "Modification and secretion of human interleukin 2 produced in insect cells by a baculovirus expression vector," *Proc. Natl. Acad. Sci.* (USA), 82:8404–8408 (Dec. 1985).

Springer et al., "The Lymphocyte Function–Associated LFA–1, CD2, and LFA–3 Molecules: Cell Adhesion Receptors of the Immune System," *Annu. Rev. Immunol.*, 5:223–252 (1987).

Springer, "Adhesion receptors of the immune system," *Nature*, 346:425-434 (Aug. 2, 1990).

Szoka, "Comparative Properties and Methods of Preparation of Lipid Vesicles (Liposomes)," *Ann. Rev. Biophys. Bioeng.*, 9:467-508 (1980).

Takehara et al., "Co-expression of the Hepatitis B Surface and Core Antigens Using Baculovirus Multiple Expression Vectors," *J. Gen. Virol.*, 69:2763-2777 (1988).

Tan et al., "Induction of Alloantigen-specific Hyporesponsiveness in Human T Lymphocytes by Blocking Interaction of CD28 with its Natural Ligand B7/BB1," *J. Exp. Med.*, 177:165-173 (Jan. 1993).

Thompson et al., "CD28 activation pathway regulates the production of multiple T-cell-derived lymphokines/cytokines," *Proc. Natl. Acad. Sci.* (USA), 86:1333-1337 (Feb. 1989).

Urakawa et al., "Synthesis of Immunogenic, but Non-infectious, Poliovirus Particles in Insect Cells by a Baculovirus Expression Vector," *J. Gen. Virol.*, 70:1453-1463 (1989).

Valle et al., "mAb 104, a new monoclonal antibody, recognizes the B7 antigen that is expressed on activated B cells and HTLV-1-transformed T cells," *Immunol.*, 69:531-535 (1990).

van Seventer et al., "Roles of multiple accessory molecules in T-cell activation," *Current Opinion In Immunology*, 3:294-303 (1991).

Van Gool et al., "CD28 Ligation by Monoclonal Antibodies or B7/BB1 Provides an Accessory Signal for the Cyclosporin A-Resistant Generation of Cytotoxic T Cell Activity," *J. Immunol.*, 150(8):3254-3263 (Apr. 15, 1993).

Vandenberghe et al., "Antibody and B7/BB1-mediated Ligation of the CD28 Receptor Induces Tyrosine Phosphorylation in Human T Cells," *J. Exp. Med.*, 175:951-960 (Apr. 1992).

Vandenberghe et al., "In situ expression of B7/BB1 on antigen-presenting cells and activated B cells: an immunohistochemical study," *Int. Immunol.* 5(3):317-321 (1993).

Verweij et al., "Activation of Interleukin-2 Gene Transcription via the T-cell Surface Molecule CD28 is Mediated through an NF-kB-like Response Element," *J. Biol. Chem.*, 266(22):14179-14182 (Aug. 5, 1991).

Warmerdam et al., "A Single Amino Acid in the Second Ig-Like Domain of the Human Fcγ Receptor II is Critical for Human IgG2 Binding," *J. Immunol.*, 147(4):1338-1343 (Aug. 15, 1991).

Warmerdam et al., "Molecular Basis for a Polymorphism of Human Fcγ Receptor II (CD32)," *J. Exp. Med.*, 172:19-25 (Jul. 1990).

Weaver and Unanue, "The costimulatory function of antigen-presenting cells," *Immunol. Today*, 11(2):49-55 (1990).

Webb et al., "Cell-surface expression and purification of human CD4 produced in baculovirus-infected insect cells," *Proc. Natl. Acad. Sci.* (USA), 86:7731-7735 (Oct. 1989).

Yokochi et al., "B Lymphoblast Antigen (BB-1) Expressed on the Epstein-Barr Virus-Activated B Cell Blasts, B Lymphoblastoid Cell Lines, and Burkitt's Lymphomas," *J. Immunol.*, 128(2):823-827 (Feb. 1982).

Young et al., "The B7/BB1 Antigen Provides One of Several Costimulatory Signals for the Activation of $CD4^+$ T Lymphocytes by Human Blood Dendritic Cells In Vitro," *J. Clin. Invest.*, 90:229-237 (Jul. 1992).

Full length B7:

Forward  MR67   5'-GCG CTGCAG CATCTGAAGCCATGGGCC-3'   (307-324)
Backward MR68   5'-CGC GGTACC TTGCTTCTGCGGACACTG-3'   (1182-1199)

Soluble B7:

Forward  MR67   5'-GCG CTGCAG CATCTGAAGCCATGGGCC-3'   (307-324)
Backward MR145  5'-GCGC GGTACC TTACTCCATGGGCATGTATTCCTCTTCCTCGTTATCAGGAAAATGCTGTTG-3'   (1022-1042)

FIG.2

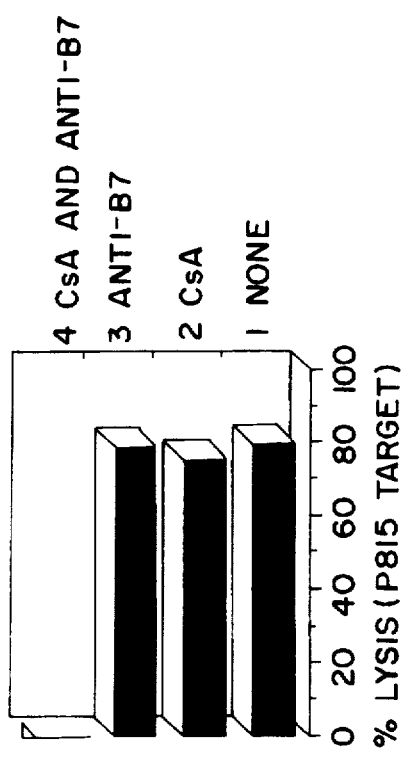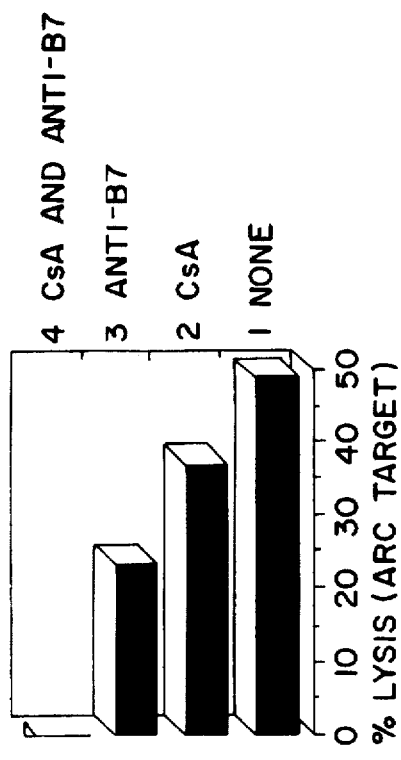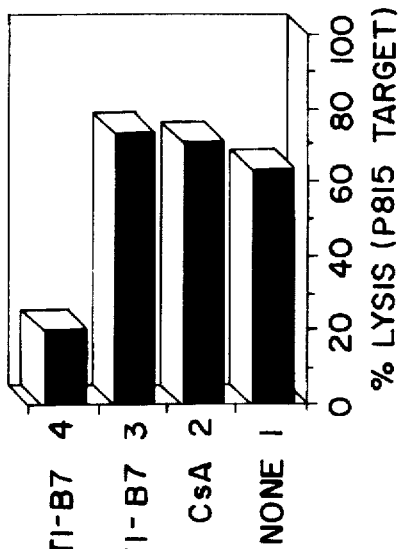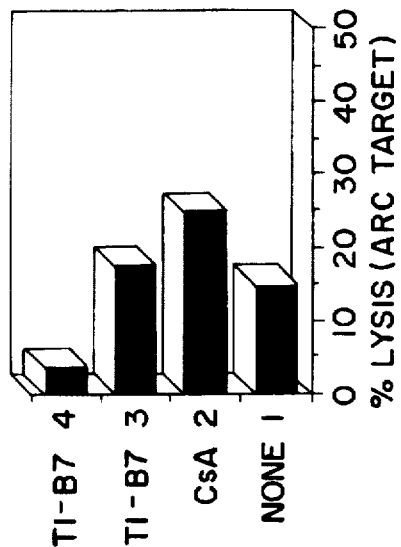

METHODS AND MATERIALS FOR THE INDUCTION OF T CELL ANERGY

This application is a continuation-in-part of U.S. application Ser. No. 08/015,147, filed Feb. 3, 1993, now pending, which is a continuation-in-part of U.S. application Ser. No. 07/910,222, filed Jul. 9, 1992, U.S. Pat. No. 5,397,703.

FIELD OF THE INVENTION

The present invention relates to methods and materials for the induction of T cell anergy. More specifically, the present invention relates to methods of preventing or treating transplant rejection, graft versus host disease, and other immunological conditions arising from the recognition of specific antigens as foreign.

BACKGROUND OF THE INVENTION

Current strategies for the prevention of graft rejection after transplantation are based on the use of broad acting immunosuppressive agents such as cyclosporin A (CsA), FK506 and corticosteroids. These drugs must often be taken over long periods of time and therefore increase the risk of serious infections, nephrotoxicity, and cancer. In addition, not all patients can tolerate high doses of these immunosuppressive agents, often resulting in graft rejection or graft-versus-host disease (GVHD). Optimal prevention of graft rejection should be based on the induction of specific tolerance to the donor tissue. Thus, the ideal drug for prevention of transplant rejection should induce clonal unresponsiveness, or anergy, of donor-reactive T cells, without the need for long-term immunosuppression. Anergy is thought to be the result of intercellular signaling after interaction between the T-cell receptor (TCR) and the peptide-presenting major histocompatibility complex (MHC) antigen in the absence of a "costimulatory" signal. Mueller et al., Annu. Rev. Immunol., 7, 445 (1989). This costimulatory signal is normally provided by the cell surface of antigen-presenting cells (APCs). Hawrylowicz et al., J. Immunol., 141, 4083 (1988); and Springer et al., Annu. Rev. Immunol., 5, 223 (1987).

T cells play an important role during the normal in vivo immune response. They are involved in cytotoxicity, delayed type hypersensitivity, and T cell-dependent antibody production by B cells. Furthermore, T cells produce a wide variety of lymphokines such as interleukin-2 (IL-2), tumor necrosis factor alpha (TNF-α), lymphotoxin, gamma interferon (IFN-γ), and granulocyte macrophage colony stimulating factor (GM-CSF).

The activation of T cells is the result of ligand-receptor interactions. Under physiological conditions, the TCR/CD3 complex binds to antigenic peptides presented by the MHC molecules of APCs. The TCR/CD3 complex plays two roles in antigen-induced activation. First, it recognizes a specific antigen in the context of an antigen-presenting MHC molecule. Then, the recognition event is transmitted through the plasma membrane by a signalling mechanism. However, binding of antigen to the TCR alone is not sufficient for maximum T cell activation. A number of other accessory molecules on the surface of the T cell play important roles in adhesion or signalling or both. For instance, the CD2 molecule on T cells binds to LFA-3 on APCs, but it has also been shown that binding of antibodies to CD2 can augment the signals provided by the TCR/CD3 complex. Other ligand pairs involved in T cell activation are LFA-1/ICAM-1, CD4/MHC-class II antigen, VLA-4/VCAM, and, most importantly, CD28/B7.

A candidate for the costimulatory signal that determines whether TCR-stimulation leads to full T cell activation or to T cell anergy is that generated by interaction of CD28 on the T cells with B7 on APCs. It is reported that in vitro cross-linking of the CD28 molecule may rescue T cells from becoming anergic. Harding et al., Nature, 356, 607 (1992). CD28 is a homodimeric transmembrane glycoprotein with an apparent molecular mass of 44 kDa and is a member of the immunoglobulin superfamily [Aruffo et al., Proc. Nat'l. Acad. Sci. (USA), 84, 8573 (1987)]. The CD28 molecule is expressed on approximately 95% of CD4-positive T cells and 50% of CD8-positive T cells. Costimulation of T cells with monoclonal antibody to the TCR/CD3 complex and CD28 results in greatly enhanced T cell activation. Thompson et al., Proc. Nat'l. Acad. Sci. (USA), 86, 1333–1337 (1989); June et al., J. Immunol., 143, 153–161 (1989); and Lindsten et al., Science, 244, 339–343 (1989). This effect apparently involves stabilization of mRNA for several lymphokines, including IL-2, resulting in a greatly enhanced production of these lymphokines. June et al., supra; and Lindsten et al., supra. Furthermore, a CD28-responsive element has been demonstrated in the enhancer of the IL-2 gene, suggesting that there is also regulation at the transcriptional level. Fraser, et al., Science, 251, 313 (1991) and Verwey et al., J. Biol. Chem., 266, 14179–14182 (1991). Certain models of T cell activation mediated by CD28 are reported to be relatively resistant to inhibition with CsA. June, et al., Mol. Cell. Biol., 7, 4472–4481 (1987)

B7 is a monomeric transmembrane glycoprotein with an apparent molecular mass of 45–65 kDa and is, like CD28, a member of the immunoglobulin superfamily. Freeman et al., J. Immunol., 143, 2714–2722 (1989). Moreover, B7-expressing CHO cells are able to synergize with TCR stimulation, resulting in IL-2 secretion and T cell proliferation. Linsley et al., J. Exp. Med., 137, 721–730 (1991); and Gimmi et al., Proc. Nat'l. Acad. Sci. (USA), 88, 6575 (1991). B7 is also reported to bind to a recombinant fusion protein of the CTLA-4 molecule. Linsley et al., J. Exp. Med., 174, 561–569 (1991). CTLA-4, too, is a member of the immunoglobulin superfamily, and the cytoplasmic regions of CTLA-4 and CD28 show significant homology. Harper et al., J. Immunol., 147, 1037 (1991). The B7 molecule is expressed on activated B cells (Freeman et al., supra), monocytes stimulated with IFN-γ [Freedman et al., Cell. Immunol., 137, 429–437 (1991)], and isolated peripheral blood dendritic cells [Young et al., J. Clin. Invest., 90, 229–237 (1992)]. Immunohistochemical studies report that the B7 molecule is constitutively expressed in vivo on dendritic cells in both lymphoid and non-lymphoid tissue. Vandenberghe et al., International Immunology (1993).

In vivo, the B7 antigen is involved in T cell activation during transplant rejection. Lenschow and co-workers have used a soluble fusion protein of human CTLA-4 and the immunoglobulin G1 Fc region (CTLA4Ig), which strongly binds to both mouse and human B7, to prevent rejection of human pancreatic islets after transplantation in mice [Lenschow et al., Science, 257, 789–792 (1992)]. Here CTLA4Ig is reported to block rejection of a xenoantigen (an antigen foreign to the species from which the T cell is derived).

Certain molecules are reported to interfere with the interaction between the B7 and CD28 antigens. The soluble CTLA4-Ig fusion protein is reported to partially block this interaction. Linsley et al., J. Exp. Med., 74, 561 (1991). Anti-CD28 antibodies are also reported to block this interaction. Furthermore, anti-B7 antibodies are known. Yokochi et al., J. Immunol., 128, 823 (1982); Freedman et al., J. Immunol., 139, 3260 (1987); Valle et al., Immunol., 69, 531 (1990).

Anergy of alloantigen-specific cytotoxic T lymphocyte precursors is reported to result from intracellular signaling after TCR/MHC interaction in the absence of a so-called costimulatory signal [Jenkins et al., *J. Exp. Med.*, 165, 302 (1987); Jenkins et al, *Proc. Nat'l. Acad. Sci. (USA)*, 54, 5409 (1987); Jenkins et al., *J. Immunol.*, 140, 3324 (1988); Mueller et al., *Ann. Rev. Immunol.*, 7, 445 (1989); and Schwartz, *Science*, 248, 1349 (1990)]. Such costimulatory signals provided by the cell surface APC reported to include CD2-LFA-3 and LFA-1 -ICAM1/2/3 interactions to re-enforce signaling through the TCR by strengthening adhesion between APC and T cells [Springer, *Nature*, 346, 425 (1990); Weaver et al. *Immunol. Today*, 11, 49 (1990) and van Seventer et al., *Current Opinion In Immunology*, 3, 294 (1991)].

One candidate for a costimulatory signal which determines whether TCR stimulation leads to full T-cell activation or T-cell anergy is the interaction of T-cell CD28 or CTLA-4 with B7 on APCs [Schwartz, *Cell*, 71, 1065 (1992) and Harding et al., *Nature*, 356, 607 (1992)]. Also of interest is that costimulation of T-cells through CD28-induces tyrosine-phorphorylation of specific substrates [Vandenberghe et al., *J. Exp. Med.*, 175, 951 (1992)], which involves a calcium-independent pathway [Thompson et al., *Proc. Nat'l. Acad. Sci. (USA)*, 86, 1333 (1989); June et al., *J. Immunol.*, 143, 153 (1989); Lindsten et al., *Science*, 244, 339 (1989); June et al., *Mol. Cell. Biol.*, 7, 4472 (1987) and Van Gool et al., *J. Immunol.*, 150, 3254 (1993)]. Stabilization of mRNA for several cytokines, including IL-2 may also be involved [Lindsten et al., *Science*, 244, 339 (1989)]. A CD28-responsive element in the enhancer of the IL-2 gene is reported [Fraser et al., *Science*, 251, 313 (1991) and Verwey et al., *J. Biol. Chem.*, 266, 14179 (1991)]. B7, the natural ligand for CD28 [Linsley et al., *J. Exp. Med.*, 173, 721 (1991) and Gimmi et al., *Proc. Nat'l. Acad. Sci. (USA)*, 88, 6575 (1991)], is reported to be a monomeric transmembrane glycoprotein with molecular mass of 45–65 kDa B7 is expressed on activated B cells, activated monocytes, and constitutively on dendritic cells in both lymphoid and non-lymphoid tissues [Vandenberghe et al., *Int. Immunol.* 5, 317 (1993)]. The B7 molecule in vivo to be involved in T-cell activation during transplant rejection. A soluble fusion protein of human CTLA-4 and the immunoglobulin CTLA-4-Ig, which strongly binds mouse and human B7, is reported to prevent rejection of human pancreatic islets after transplantation in mice [Lenschow et al., *Science*, 257, 789 (1992)]. A specific hyporesponsiveness is reported to be induced in human T cells after blocking the B7-CD28/CTLA-4 and activation with alloantigens [Tan et al., *J. Exp. Med.* 177, 165 (1993)]. T-cell activation mediated by CD28 is reported to be resistant to inhibition with CsA under certain conditions [June et al., *Mol. Cell. Biol.*, 7, 4472 (1987) and Van Gool et al., *J. Immunol.*, 150, 3254 (1993)]. With respect to whether the presence of CsA and a mAb against the B7 molecule induces persisting unresponsiveness or anergy of human CTL-precursors, T-cell anergy was studied at the cytotoxic effector level, which was selected as being most relevant for transplant rejection and most difficult to induce [Otten et al., *Science*, 251, 1228 (1991) and Go et al., *J. Immunol*, 150, 367 (1993)].

SUMMARY OF THE INVENTION

The current invention is also based on the discovery that the coadministration of a molecule that binds to the B7-1 antigen and an immunosuppressive agent to a patient induces long-lasting T cell anergy against an alloantigen (an antigen native to the same species as the T cell).

Accordingly, this invention provides a method for preventing transplant rejection in a patient, the method comprising administering to a patient in need of such treatment therapeutically effective amounts of (1) a molecule that binds to the B7-1 antigen and (2) an immunosuppressive agent such as cyclosporin A, FK506, or a corticosteroid, in a pharmaceutically acceptable excipient. In a preferred embodiment of this invention, the molecule that binds to the B7-1 antigen is an anti-B7-1 antibody.

Additionally, this invention provides a method for preventing or treating graft versus host disease (GVHD) in a patient, the method comprising administering to a patient in need of such treatment therapeutically effective amounts of (1) a molecule that binds to the B7-1 antigen and (2) an immunosuppressive agent such as cyclosporin A, FK506, or a corticosteroid, in a pharmaceutically acceptable excipient. In a preferred embodiment of this invention, the molecule that binds to the B7-1 antigen is an anti-B7-1 antibody.

Also, this invention provides a method for preventing or treating rheumatoid arthritis in a patient, the method comprising administering to a patient in need of such treatment therapeutically effective amounts of (1) a molecule that binds to the B7 antigen and (2) an immunosuppressive agent such as cyclosporin A, FK506, or a corticosteroid, in a pharmaceutically acceptable excipient. In a preferred embodiment of this invention, the molecule that binds to the B7-1 antigen is an anti-B7-1 antibody.

In more preferred embodiments of the above methods, the anti-B7-1 antibody is a monoclonal antibody, most preferably the B7-24 monoclonal antibody, made as described herein.

BRIEF DESCRIPTION OF THE FIGURES

FIG. 2 shows the sequences of polymerase chain reaction primers used in the preparation of coding regions for human human B7-1 antigens. These primers were constructed on the basis of the published complete DNA coding sequences for antigens B7-1 (Freeman et al., 1989).

In FIGS. 11A–D. bar graphs illustrate synergy between mAb B7-24 and CsA in blocking the primary MLR and in the induction of persistent alloantigen-unresponsiveness of CTL-precursors.

DETAILED DESCRIPTION OF THE INVENTION

Figure 1A:
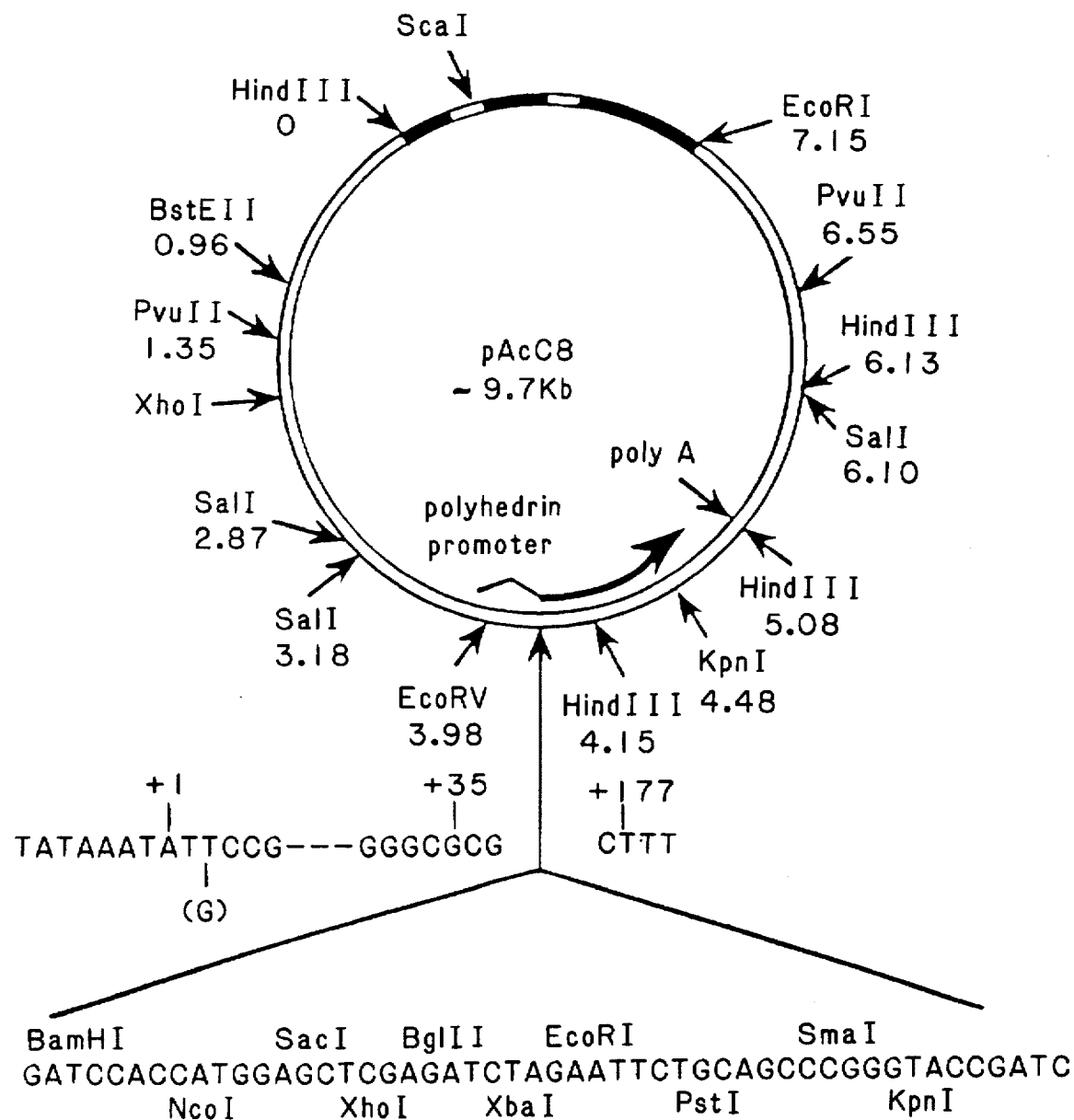
FIG. 1A shows a schematic representation of the baculoviral transfer vector pAcC8 and the sequence of the multiple cloning site.

The invention described herein draws on previously published work and pending patent applications. By way of example, such work consists of scientific papers, patents or pending patent applications. All of these publications and applications, cited previously or below are hereby incorporated by reference.

The optimal therapy to prevent graft rejection should be based on the induction of specific tolerance to the donor tissue. Current concepts on immunological tolerance hold that anergy is the result of intercellular signaling after TCR/MHC-peptide interaction, in the absence of a so-called co-stimulatory signal (Jenkins et al., *J. Exp. Med.*, 165, 302 (1987)). This co-stimulatory signal is provided by the cell surface of antigen presenting cells (APC). At present, the best candidate co-stimulatory signal that determines whether TCR-stimulation leads to full T-cell activation or T-cell tolerance, is generated by ligation of the CD28 molecule on the T cells (Harding et al., *Nature*, 356, 607). It has been demonstrated that there are at least 2 ligands for the CD28 molecule on professional APC, named B7-1 and B7-2 (Freeman et al., *Science*, 262, 909 (1993)). It is known that both these molecules can provide a co-stimulatory signal for the activation of T cells.

Monoclonal antibody B7-24 is an unique monoclonal antibody that binds specifically to the B7-1 molecule, but not to B7-2. This is in contrast with a recombinant fusion protein of the CTLA-4 molecule (Linsley, *J. Exp. Med.*, 174, 561 (1991), which binds to both B7-1 and B7-2. Monoclonal antibody B7-24 is also different from the anti-B7 monoclonal antibody BB-1, which binds to B7-1 and in addition to a third form of the B7 molecule, B7-3 (Boussiotis et al., *Proc. Nat'l. Acad. Sci. (USA)*, 90, 11059 (1993)). Although it is known that both B7-1 and B7-2 can co-stimulate T cells by binding to the CD28 molecule, it is not known that blocking only B7-1 with a specific monoclonal antibody such as B7-24, when combined with an immunosuppressive drug such as cyclosporin A, can induce T-cell tolerance or anergy. This is unexpected since it has been suggested in the literature that CsA can prevent anergy induction in mice [Schwartz, *Science*, 248, 425 (1990)].

Without limitation to a proposed mechanism the tolerance induction by mAb B7-24 and CsA may be explained as follows. The induction of tolerance is an active process, which means that it requires activation of certain genes and production of the corresponding proteins by T cells. These genes ("anergy genes") are activated when the TCR/CD3 complex on the T cell are stimulated with the specific antigen. During transplantation this is the alloantigen and this may be considered as signal 1. Activation of T cells by (allo)antigen takes place upon interaction with APC, which at the same time provide co-stimulatory signals via molecules such as the B7 molecules. this may be considered as signal 2. When T cells receive both signal 1 and signal 2, not only the anergy genes are activated, but also the genes for T-cell growth factors such as IL-2. These T-cell growth factor on their turn may bind to specific receptors on the T cells (IL-2 receptors) and will result in full activation of the T cells. apparently over-riding or inactivating the anergy genes.

Immunosuppressive drugs, such as CsA. may partially inhibit the activation of the IL-2 gene. but in humans do not prevent the activation of the anergy genes. However, when CsA is used alone, it does not completely inhibit the production of IL-2 and the production of small amounts of IL-2 inactivates the anergy genes.

Given that both B7-1 and B7-2 may provide the co-stimulatory signal to T cells for the production of IL-2, it is surprising that blocking only B7-1 in combination with CsA results in T-cell tolerance. This may be explained by the fact that it is known that signal transduction after cross-linking of CD28 results in two independent signaling pathways, one being CsA-sensitive and one being CsA-insensitive. It may be that signal transduction after interaction of CD28 with B7-2 is mediated by the CsA-sensitive pathway. In addition, in light of recent experiments [Lin et al., *J. Exp. Med.*, 178, 1801 (1983)] it may be proposed that signal transduction after interaction of B7-2 with CD28 is needed for the induction of the anergy genes. Therefore co-administration of a molecule that specifically binds to the B7-1 molecule but not to B7-2 or B7-3 and an immunosuppressive agent that inhibits the production of IL-2 by T cells to a patient may induce long-lasting T-cell tolerance or anergy.

In order to induce long-lasting transplantation tolerance, patients receiving transplantation may receive a prophylactic treatment consisting standard immunosuppressive therapy and a short treatment course with the anti-B7-1 monoclonal antibody B7-24. Standard immunosuppressive therapy usually consists of Cyclosporin A given at a starting dose of 6 mg/kg/day, adjusted to maintain whole-blood levels between 150 and 250 ng/ml. Dipyridamole and acetylsalicylic acid may be given in association with CsA. In addition, patients may receive azathioprine and steroids. Where the initially high doses of steroid is tempered off to low maintenance doses. The first dose of monoclonal antibody B7-24 is administered to the patients between 1 and 6 hours before surgery. The other doses are given daily on day 1–10 post-transplantation. After day 10 the patients may receive standard immunosuppressive treatment, whereby to doses of the immunosuppressive drugs are slowly tempered to low maintenance levels or taken completely off immunosuppressive drug treatment.

I. Definitions

As used herein, the term "membrane-associated antigen", "cell surface molecule" and "cell surface antigen" all refer to a protein, polypeptide or peptide, where at least one antigenic portion of the protein, polypeptide or peptide is exposed on a surface of a biological membrane and which may have one or more of the following moieties covalently attached: one or more simple or complex sugar moieties (as in a glycoprotein), lipid moieties (as in a lipoprotein), a combination of lipid and sugar moieties, or other post-translational modifications.

"Proteins" are typically long chains of amino acid based polymers ("polypeptides"). Proteins may be composed of one, two or more polypeptide chains and may further contain some other type of substance in association with the polypeptide chain(s), such as carbohydrates. The size of proteins covers a rather wide range from (an arbitrary figure of) 5,000 to several hundred thousand g/mole. The 5,000 figure corresponds to the presence of roughly 40–45 amino acids. Proteins smaller than about 5,000 g/mole are typically referred to as polypeptides or simply peptides (Bohinski).

As used herein, the term "antibody" refers to polyclonal antibodies, monoclonal antibodies, humanized antibodies, single-chain antibodies, and fragments thereof such as $F_{ab}$, $F_{(ab')2}$, $F_v$, and other fragments which retain the antigen binding function of the parent antibody.

As used herein, the term "monoclonal antibody" refers to an antibody composition having a homogeneous antibody population. The term is not limited regarding the species or source of the antibody, nor is it intended to be limited by the manner in which it is made. The term encompasses whole immunoglobulins as well as fragments such as $F_{ab}$, $F_{(ab')2}$, $F_v$, and others which retain the antigen binding function of the antibody. Monoclonal antibodies of any mammalian species may be used in this invention. In practice, however, the antibodies are typically of rat or murine origin because of the availability of rat or murine cell lines for use in making the required hybrid cell lines or hybridomas to produce monoclonal antibodies.

As used herein, the term "humanized antibodies" means that at least a portion of the framework regions of an immunoglobulin are derived from human immunoglobulin sequences.

As used herein, the term "single chain antibodies" refer to antibodies prepared by deter-mining the binding domains (both heavy and light chains) of a binding antibody, and supplying a linking moiety which permits preservation of the binding function. This forms, in essence, a radically abbreviated antibody, having only that part of the variable domain necessary for binding to the antigen. Determination and construction of single chain antibodies are described in U.S. Pat. No. 4,946,778 to Ladner et al.

As used herein, the term "molecule which binds to the B7-1 antigen" means a molecule which is capable of forming a complex with the B7-1 antigen in an environment wherein other substances in the same environment are not complexed to the B7-1 antigen. The complex is formed in a manner that blocks the normal signal transduction pathway of B7-1 through the CD28 or CTLA4 antigen. Molecules which bind to the B7 antigen include CD28, CTLA4, CTLA4Ig and anti-B7 antibodies.

II. Generating Antibodies to Membrane-Associated Antigen Molecules

This section describes a method for generating and selecting antibodies to a cell surface molecule, using transfected insect cells as immunogens. The method involves the following steps: the immunization step, which includes (i) selecting and isolating a nucleic acid coding sequence which encodes the antigen of interest, (ii) inserting the coding sequence into a baculoviral expression vector so as to obtain efficient expression of the coding sequence, (iii) transfecting the expression vector into an insect cell line to obtain recombinant insect cells expressing the selected antigen, and (iv) immunizing a host animal with the insect cells expressing the membrane-associated antigen.

After immunization, the serum of the host animal is screened against cells, other than the insect cells, expressing the antigen of interest. Alternatively, membrane fractions containing the antigen of interest, or in some cases, purified recombinantly-produced antigens themselves may be used to screen the serum. Typically, (a) pre-bleed serum, (b) the serum of a host animal immunized with insect cells not expressing the antigen of interest, and (c) the serum of the host animal immunized with the recombinant insect cells are screened. The presence of antibodies specifically directed against the antigen of interest is indicated by negative reactions with sera (a) and (b), and positive reactions with serum (c).

Hybridomas which produce monoclonal antibodies to a cell surface protein may also be generated. The method involves the steps (i) to (iv) described above. After immunization of the host animal with the recombinant insect cells, antibody-producing cells are isolated from the animal. Such antibody-producing cells may be used to generate hybridoma cells, which are cloned and used for the production of monoclonal antibodies. Supernatants from such hybridoma cells are screened for specific antibody production, for example, using a cell-based screening assay described below.

A. Isolating Coding Sequences for Membrane Molecules

The nucleic acid coding sequence for a selected membrane-associated antigen may be isolated based on known amino acid and/or DNA coding sequences for the protein component of the antigen. The coding sequence can be isolated from biological sources by standard procedures [Ausubel, et al.; Maniatis, et al.; Sambrook, et al.] (e.g., hybridization, differential hybridization, cloning and plaque screening, etc.). Alternatively, synthetic oligonucleotide sequences encoding the antigen of interest may be prepared using commercially available automated oligonucleotide synthesizers or may be purchased, for example, from Synthetic Genetics (San Diego, Calif.). In the case of large coding sequences, the oligonucleotide coding sequence can be synthesized through a series of cloning steps involving a tandem array of multiple oligonucleotide fragments corresponding to the coding sequence [Crea; Yoshio et al.; Eaton et al.]. Oligonucleotide coding sequences may be amplified and isolated by standard recombinant procedures [Maniatis et al.; Ausubel et al.] or by polymerase chain reaction [Mullis; Mullis, et al.].

When the sequence of the membrane-associated antigen is known or partially known a specific antigen coding sequence may be isolated. Typically, the antigen coding sequence is isolated from a cDNA library, generated by the insertion of DNA fragments from a selected source into a vector. The cDNA library containing DNA fragments from a membrane antigen-containing source can be constructed using random fragments cDNA molecules generated from target RNA molecules. Such a cDNA library is generally constructed using a bacterial system (such as lambda gt10 (Promega, Madison, Wis.), but can also be constructed in a yeast or eukaryotic expression system using conventional techniques (Ausubel).

The library is screened (usually by hybridization; Ausubel, et al.; Maniatis, et al.) for the presence of the membrane-associated antigen DNA sequence, typically using as a probe an oligonucleotide having a known or consensus sequence hybridizable with the antigen coding region. The probe can carrying a number of detection moieties including radioisotopes, biotin and digoxigenin. Alternatively, when a nucleic acid probe sequence is not available, screening for clones carrying the coding region of interest can be carried out using, for example, immunoscreening (using "PROTOCLONE" lambda gt11 system, Promega; Young, et al.; Huynh, et al.).

Coding regions are isolated from recombinant isolates giving positive signals (either by hybridization or immunological screening). Typically, DNA fragments containing the coding regions are isolated by restriction digestion followed by size fractionation and fragment purification. Such nucleic acid coding regions may then be processed for insertion into a baculoviral transfer vector, such as the vector pAcC8 (FIG. 1A), as described in part B, below. Alternative baculovirus vectors are available including the vectors pVL1393 (Luckow et al.) and pAC3T3 (Summers et al.).

Alternately, coding sequences can also be isolated using polymerase chain reaction (PCR) amplification (Mullis; Mullis, et al.). Primers useful for the PCR can be derived from any known nucleic acid sequence. If the exact sequence is not known degenerative primers can be used (Mullis; Mullis, et al.). Typically these primers are two nucleic acid sequences consisting of 8 or more colinear nucleotides, where the two sequences are separate by some defined distance, in order to generate a target sequence (Example 1), and are complementary to opposite strands.

A typical PCR cycle involved the following steps: melting at elevated temperature, followed by annealing, and extension. The reactions are repeated for 25–30 cycles. The PCR products can be digested with restriction enzymes and electrophoretically resolved using a preparative 1.5% agarose gel. Clone-specific, amplified fragments are typically identified by electrophoretic gel size fractionation. The clone-specific DNA fragments are then recovered from the gel, for example, using the "GENE CLEAN" system (BIO 101, La Jolla Calif.). If necessary the DNA can be extracted with phenol and/or phenol:chloroform (1:1). Isolated DNA is ethanol precipitated. Following precipitation, the DNA is used for insertion into baculovirus expression vectors.

Figure 1B:
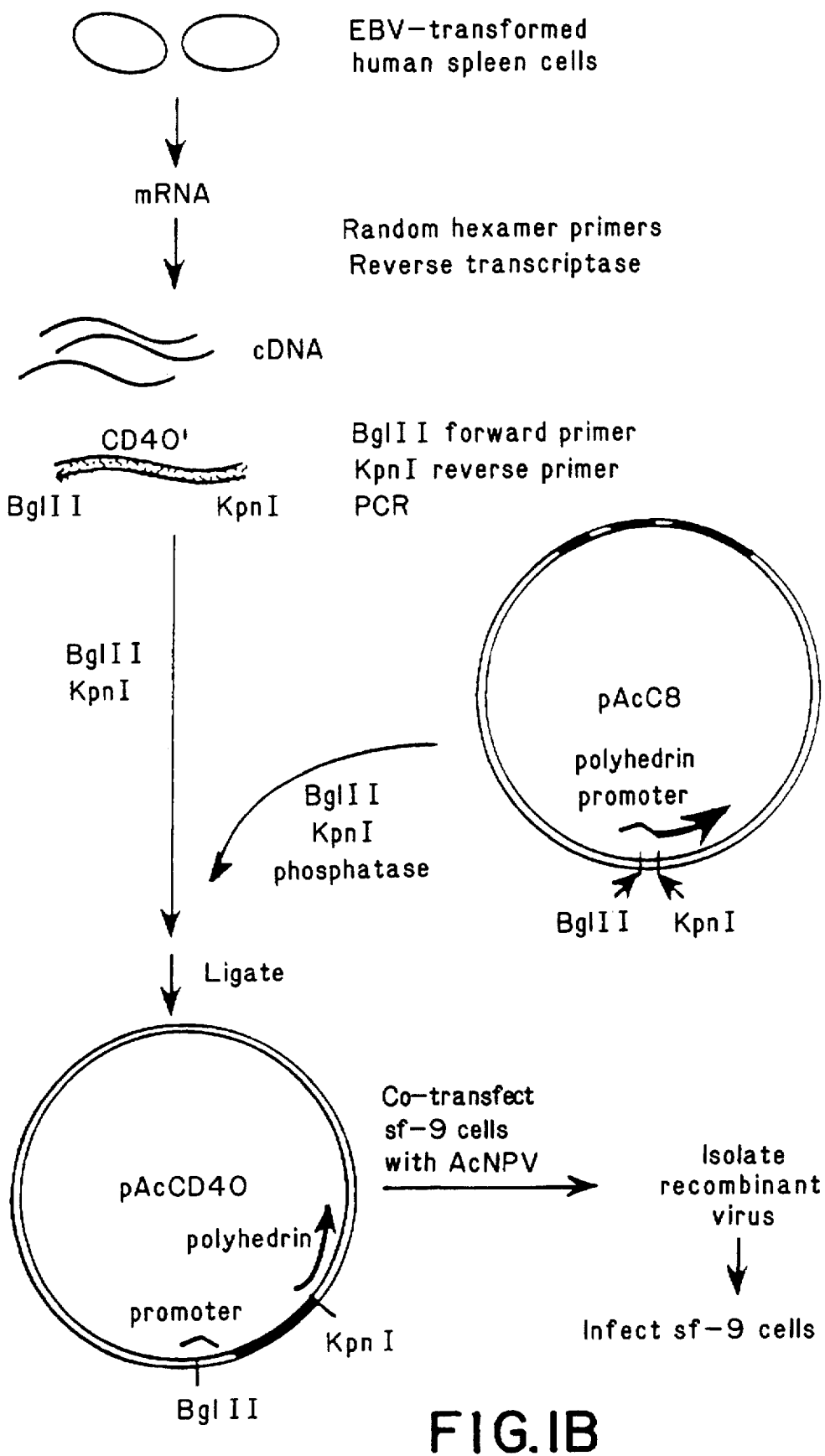
FIG. 1B shows a schematic representation of the generation of Sf9 cells which express human B7-1 antigen according to the the present invention.

The generation of Sf9 cells expressing human B7-1 antigens is schematically shown in FIG. 1B. As shown, RNA is isolated from a population of Epstein-Barr virus (EBV)-transformed human spleen cells, using standard procedures (Chirgwin, et al.). Total RNA is converted to cDNA using random hexamer priming, according to established methods, and as detailed in Example 1. The DNA molecule encoding the membrane-associated antigen molecules of interest is generated by PCR amplification, using forward and reverse primers having restriction sites for cloning at their 5' termini. Such cDNA primers, used in the preparation of coding regions for human B7-1 antigens are depicted in FIG. 2. These primers were constructed on the basis of the published complete DNA coding sequences for antigens B7 (Freeman et al., 1989).

With continuing reference to FIG. 1B, the cDNA is mixed with a forward primer and a reverse primer, in the presence of a thermostable polymerase, such as polymerase obtained from *Thermus aquaticus*, a mixture of equimolar deoxynucleotides, and a buffer system (Example 1). The mixture is subjected to amplification in a thermocycler, and PCR products obtained are subcloned in the polylinker of a baculovirus transfer vector. One such vector, pAcC8, is diagrammatically represented in FIG. 1A. Any of a number of such baculoviral transfer vectors containing unique restriction endonuclease sites downstream of the polyhedrin promoter (Miller) can be utilized in the practice of the present invention: for *Autographica californica* nuclear polyhedrosis virus (AcNPV) (Wu, et al.; Matsuura, et al.; Takehara, et al.) or *Bombyx mori* nuclear polyhedrosis virus (pBmNPV) polyhedrin MRNA (Nyunoya, et al.; Sekine, et al.).

Before expression in baculovirus, DNA inserts are typically checked for PCR-induced mutations by sequencing analysis.

B. Inserting an Antigen Coding Sequence into a Baculoviral Vector

Insertion of the membrane-associated antigen coding region into a baculovirus vector is performed according to established procedures [Ausubel, et al.; Maniatis, et al.; Sambrook, et al.]. Full length cDNAs encoding human B7-1 and human CD40 were generated by PCR using primers with restriction sites for cloning. The template for PCR amplification was cDNA generated from EBV-transformed human spleen B cell RNA. Briefly, an isolated DNA coding region is ligated into the baculoviral transfer vector or plasmid, such as a pAcC8 plasmid, so tha t the membrane-associated coding region is down-stream of the polyhedron promoter. The polyhedron gene ATG has been mutated to ATT (FIG. 1A) to prevent translational initiation in recombinant clones that do not contain a coding sequence with a functional ATG. The resulting plasmid DNA is co-transfected with wild type baculovirus (ACNPV) into insect cells from Spodoptera frugiperda (Sf9 cells) to create recombinant virus particles, via in vivo recombination between the wild type virus and the recombinant vector, carrying the membrane-associated antigen gene.

Examples 1–2 describe the isolation of recombinant baculovirus vectors containing heterologous segments of DNA: pAcB7 (encoding a full-length B7 molecule) and pCcB7-ED/Glu (encoding the cellular domain of the B7-1 molecule).

C. Infecting Insect Cells with Baculoviral Vectors

The recombinant viruses described above were then used to co-infect insect cells (Example 2). These cells then expressed the antigens encoded by the heterologous DNA inserts.

Sf9 cells (*Spodoptera frugiperda*; Summers, et al.), at a density of 106 cells/ml, were infected with recombinant virus. Recombinant baculovirus-infected Sf9 cells were identified and clonally purified (Summers et al.).

Cells expressing cell surface antigen were harvested after 48 hours and used for the immunization of host animals. For production of secreted recombinant proteins, the cells were harvested after 72 hours of culture.

Figure 3:
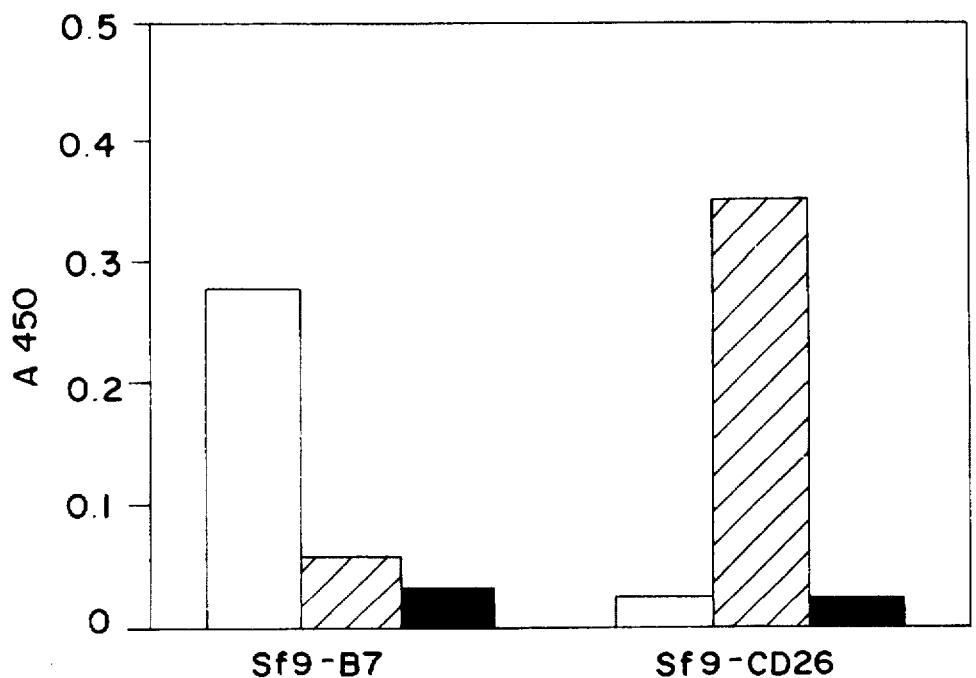
FIG. 3 shows the results of ELISA assays examining the reaction of anti-(B7) monoclonal antibody BB-1 with Sf9 cells infected with AcB7 virus and with Sf9 cells expressing human CD26.

The expression of the recombinant molecules on the cell surface of the Sf9 cells (Example 3) was tested using an ELISA system (Harlow, et al.). FIG. 3 shows that the anti-(B7) monoclonal antibody BB-1 reacted only with Sf9 cells infected with AcB7 virus, but not with Sf9 cells expressing human CD26.

D. Injecting Insect Cells Expressing the Membrane-Associated Antigen into a Host Animal Appropriate host animals for the production of polyclonal antibodies include, for example, rabbits, goats, sheep, guinea pigs, chimpanzees and dogs. One advantage of the present invention is that immunization adjuvants are generally not required.

Appropriate host animals for use in the production of monoclonal antibodies commonly include rats, hamsters and mice. However, in cases where it is desirable to produce antibodies that are immunologically closer to humans, sources of such antibodies may include higher primates such as chimpanzees. Fusion with a heteromyeloma fusion partner can be used for the generation of monoclonal antibodies (Carroll; Perkins, 1991). Such fusions may be achieved by a number of methods known in the art (Harlow, et al.) including exposure of mixed cells to polyethylene glycol and exposure of cells to strong electric field (electrofusion).

Hybridomas are selected by growth in selective medium, then are tested for antigen specificity as described below.

Figure 4:
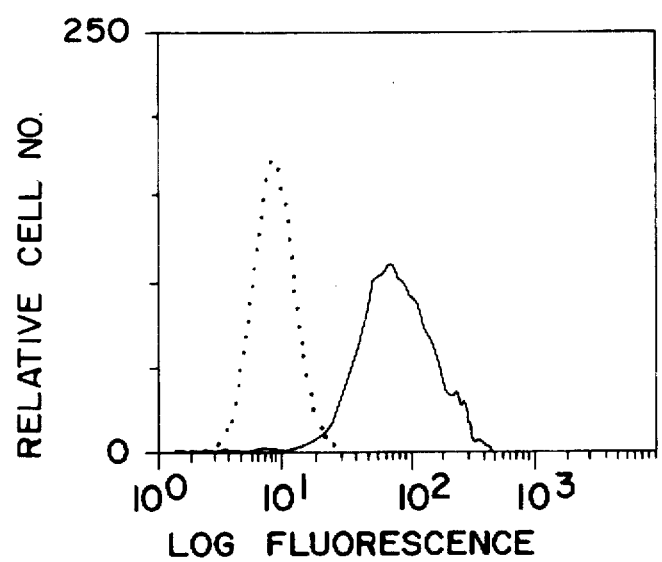
FIG. 4 shows the results of the fluorescent cell staining of EBV-transformed B cell line ARC cells expressing B7-1.
Figure 5A:
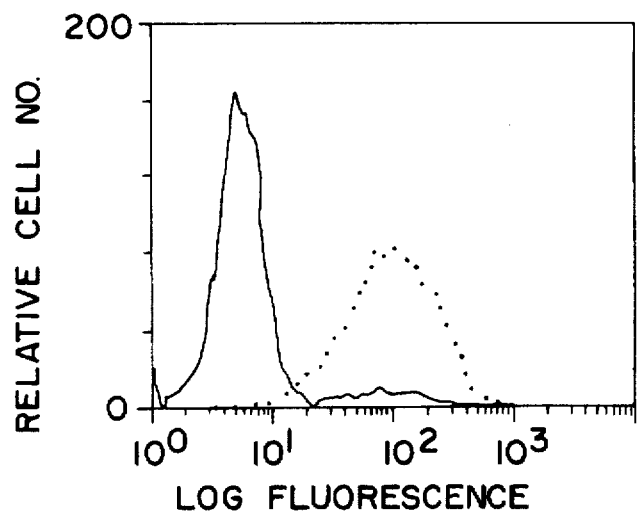
FIG. 5 A and B assays using fluorescent cell staining of EBV-transformed B cell line ARC cells expressing CD40 and B7-1, as well as soluble B7-1 antigens.
Figure 5B:
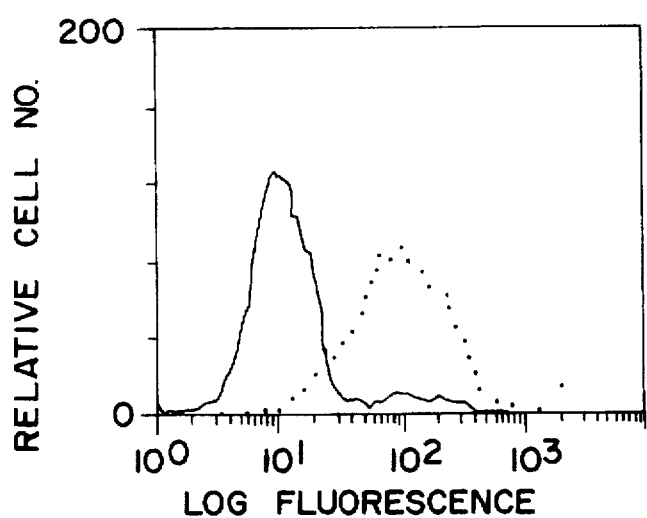

For the generation of monoclonal antibodies to CD40 and B7-1, mice were immunized (Example 5) with the Sf9 cells expressing these molecules on the cell surface. One week after the second immunization, the mice were bled and the sera were analyzed for the presence of specific antibodies using fluorescent cell staining of EBV-transformed B cells (Example 3). FIG. 4 shows the results of the cell staining which indicate that mice immunized with Sf9 cells expressing B7 had a serum titre against EBV-transformed B cell line ARC (American Type Culture Collection (A.T.C.C.), 12301 Parklawn Dr., Rockville Md. 20852), which is positive for both CD40 and B7. In contrast, mice which were immunized with control Sf9 cells showed no reactivity with the ARC cells. The results indicate that host animals can be immunized with Sf9 cells expressing a membrane-associated antigen of choice and the immunization results in an immune response including antibodies against the recombinant antigen. The immunization does not result in antibodies cross-reactive with human proteins other than the recombinant human protein cloned in the Sf9 insect cells.

One mouse was given a final booster injection with CD40 expressing Sf9 cells and one with B7-1 expressing Sf9 cells. Three days after the booster injection, the spleens were removed and the splenocytes were fused with SP2/0 murine myeloma cells.

E. Isolating and Immortalizing Specific Antibody-Producing Lymphocytes

Antibody-producing lymphocytes for monoclonal antibody production are preferably B-lymphocytes, such as may be isolated from the bone marrow, spleen or lymph nodes of an immune host animal (Harlow, et al.).

Alternatively, B-lymphocytes may be isolated from the peripheral circulation. In this case, blood samples are centrifuged, and are subjected to gradient separation techniques to produce a crude peripheral blood lymphocyte (PBL) mixture. Monocytes and T-lymphocytes are selectively depleted from this cell mixture according to established procedures (Mishell). Such remaining cells may be subjected to a selection procedure, such as a "panning" procedure, in which those cells having affinity for the antigen are concentrated by selective capture by an affinity matrix containing the antigen. In the context of the present invention, such a matrix may comprise a cell which expresses the membrane-associated antigen.

When B-lymphocytes are isolated from the circulation as described above, transformation with a transforming virus, such as Epstein-Barr virus, may be advantageous. Transformed cells (lymphoblastoids) are dispensed in subculture wells and maintained in culture for several weeks, prior to testing for specific antibody production. Cultures exhibiting such specific antibody production are expanded and fused with species-appropriate myeloma partner cells using one or more standard fusion protocols, including polyethylene glycol, as described above, or electrofusion. Methods for isolation and immortalization of B-lymphocytes from various sources are known in the art.

In experiments carried out in support of the present invention, splenocytes from immunized mice were fused with SP2/0 murine myeloma cells polyethylene glycol as described by de Boer et al. (1988). The hybridoma clones were processed as described in Example 6.

Table 1 (Example 6) gives a summary of the fusion data. After the B7 fusion, the cells were distributed in 960 wells and this fusion yielded 312 wells with hybridoma growth. Fourteen days after the fusions, supernatants of 12 wells were pooled and the pools were tested for the presence of antibodies reactive with ARC cells. FACS analysis revealed that 1 pool from the B7-1 fusion was reactive with ARC cells. When individual supernatants from the positive pools were retested, 1 well reactive with B7 was identified. The cells from this positive well were cloned by limiting dilution, and, after 3 rounds of cell growth, 1 stable anti-(B7) hybridoma clone (HB 11341) was established. These results indicate the ability to achieve stable hybridoma clones secreting monoclonal antibodies directed against a chosen membrane-associated antigen.

A number of methods for screening hybridoma fusions are available (Harlow, et al.), including: antibody capture, (i) using labeled antigen, e.g., radioactively labelled partially purified or purified antigen, (ii) whole or permeabilized cells, e.g., Sf9 cells expressing the recombinant antigen; and antigen capture, (i) antibody/antigen in solution, (ii) antibody/antigen solid phase.

F. Testing the Specificity of the Monoclonal Antibodies

EBV-transformed cells were used for the screening of the primary hybridoma supernatants and for screening of the subsequent products of the limiting dilution cloning. Several lines of evidence presented below support the fact that 1 anti-(B7-1) monoclonal antibodies have been generated.

First, supernatants from all 5 hybridoma clones were reactive with ARC cells and other EBV-transformed B cell lines, but not with T cell lines HSB (A.T.C.C.) and CEMM (A.T.C.C.).

Figure 6:
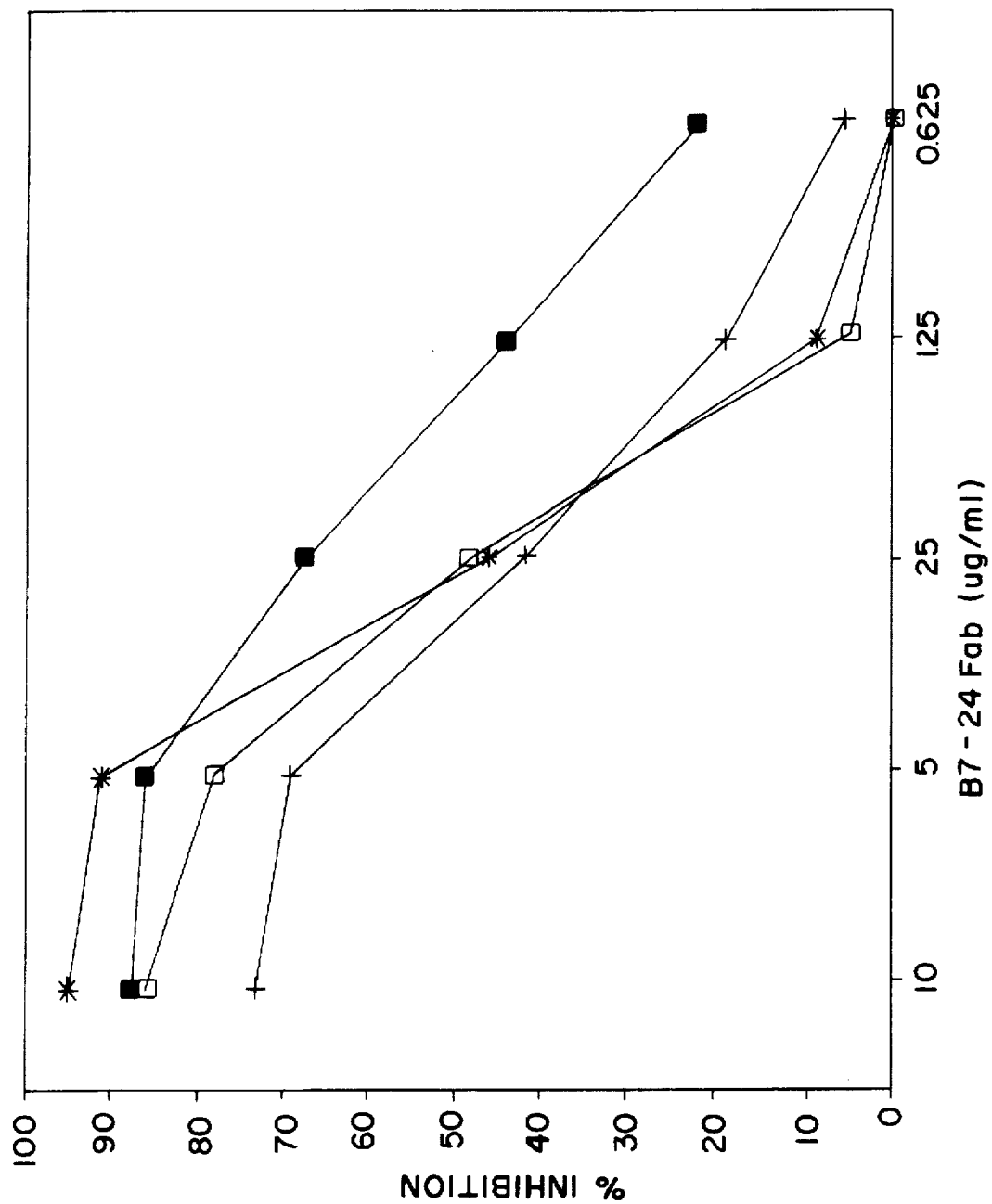
FIG. 6 shows the inhibition of anti-CD3-induced, B7-mediated proliferation of T cells by Fab fragments of anti-B7-1 Mab B7-24.

Second, competition binding experiments were performed using the monoclonal antibodies of the present invention and soluble forms of the target antigens (Example 7). Hybridoma supernatants were pre-incubated with a soluble form B7-1 (Example 7). Subsequently, the mixtures were added to ARC cells for fluorescent cell staining. The results of the competition experiment are shown in FIG. 6. The data show that soluble B7-1, blocks the binding of anti-(B7-1) monoclonal antibody B7-24 to ARC cells. Furthermore, the effect of soluble B7-1 on the anti-(B7-1) monoclonal antibody was concentration dependent. Decreasing the amount of soluble protein resulted in decreased blocking of binding of the antibodies to ARC cells.

For further analysis, the anti-(B7-1) monoclonal antibody was tested for its ability to bind to tonsillar B cells (Example 8). Table 2 shows that 12–17 percent of freshly isolated tonsillar B cells stained positive with anti-(B7-1) monoclonal antibody B7-24. However, when tonsillar B cells were cultured for 5 days in the presence of immobilized anti-(IgM) antibodies and IL-2, the percentage of cells positive for B7-24 increased up to about 25 percent.

Furthermore, when tonsillar B cells were stimulated with anti-(IgM) antibodies and IL-2, not only did the number of B cells positive for B7-24 increase, but there was also a significant increase in the amount of fluorescent staining per cell, indicating that the expression of B7-1 was increased after stimulation.

The monoclonal antibodies obtained by the method of the present invention can be typed as previously described (Harlow, et al.).

For the production of monoclonal antibodies it is optimal to immunize mice with purified material. However, purification of membrane antigens requires specialized and complex techniques, and furthermore, extraction from the membrane may alter the structure of the molecule. In addition, solubilization of proteins often decreases their immunogenicity. Therefore, most monoclonal antibodies to cell surface antigens have been obtained after immunization with mice with whole cells or membrane fractions. In many cases, specific lymphocyte subsets have been injected into mice resulting in panels of monoclonal antibodies. These antibodies have been used to isolate and characterize the antigen that they bound. When mice are immunized with whole cells, antibodies to a large number of different molecules are generated. It is therefore difficult to use the same cells for the screening of specific antibody production by the hybridoma clones.

To circumvent the above-mentioned problem, the above method involves the expression of membrane-associated antigens in insect cells and the use of these insect cells to immunize host animals. Since the introduction of PCR technology (Saiki et al., 1985; Saiki et al., 1988; Mullis; Mullis, et al.), it has become relatively straight-forward to clone cDNAs for proteins whose coding nucleic acid coding sequence has been published. One may use PCR primers spanning the complete coding region only, and incorporate restriction sites in these primers to facilitate cloning into expression vectors.

Antibodies obtained by the method of the present invention, directed against membrane-associated antigens, are advantageous for use as diagnostic agents for the detection of the membrane-associated antigen. For example, antibodies directed against cell-surface marker proteins or viral proteins protruding from the cell surface.

Compositions Using Antibodies

This invention contemplates the use of antibodies such as those made by the above-described method. The antibodies of the current invention bind to the B7 antigen. These antibodies may, however, be polyclonal antibodies, monoclonal antibodies, humanized antibodies, single-chain antibodies, and fragments thereof. The anti-B7-1 antibodies may be used in a composition that also contains an immunosuppressive agent.

A. Antibody Preparation

Monoclonal antibody B7-24 is prepared as in section II of the detailed description and Examples herein.

1. Polyclonal Sera

Polyclonal sera may be prepared by conventional methods. In general, a solution containing the B7 antigen is first used to immunize a suitable animal, preferably a mouse, rat, rabbit or goat. Rabbits and goats are preferred for the preparation of polyclonal sera due to the volume of serum obtainable, and the availability of labeled anti-rabbit and anti-goat antibodies. Immunization is generally performed by mixing or emulsifying the antigen-containing solution in saline, preferably in an adjuvant such as Freund's complete adjuvant, and injecting the mixture or emulsion parenterally (generally subcutaneously or intramuscularly). A dose of 50–200 µg/injection is typically sufficient. Immunization is generally boosted 2–6 weeks later with one or more injections of the protein in saline, preferably using Freund's incomplete adjuvant. One may alternatively generate antibodies by in vitro immunization using methods known in the art, which for the purposes of this invention is considered equivalent to in vivo immunization.

Polyclonal antisera are obtained by bleeding the immunized animal into a glass or plastic container, incubating the blood at 25° C. for one hour, followed by incubating at 4° C. for 2–18 hours. The serum is recovered by centrifugation (e.g., 1,000×g for 10 minutes). About 20–50 ml per bleed may be obtained from rabbits.

2. Monoclonal Antibodies

Monoclonal antibodies are prepared using the method of Kohler and Milstein, Nature, 256, 495–96 (1975), or a modification thereof. Typically, a mouse or rat is immunized as described above. However, rather than bleeding the animal to extract serum, the spleen (and optionally several large lymph nodes) are removed and dissociated into single cells. If desired, the spleen cells may be screened (after removal of nonspecifically adherent cells) by applying a cell suspension to a plate or well coated with the protein antigen. B-cells expressing membrane-bound immunoglobulin specific for the antigen bind to the plate, and are not rinsed away with the rest of the suspension. Resulting B-cells, or all dissociated spleen cells, are then induced to fuse with myeloma cells to form hybridomas, and are cultured in a selective medium (e.g., hypoxanthine, aminopterin, thymidine medium, "HAT"). The resulting hybridomas are plated by limiting dilution, and are assayed for the production of antibodies which bind specifically to the desired immunizing cell-surface antigen (and which do not bind to unrelated antigens). The selected mAb-secreting hybridomas are then cultured either in vitro (e.g., in tissue culture bottles or hollow fiber reactors), or in vivo (as ascites in mice).

If desired, the antibodies (whether polyclonal or monoclonal) may be labeled using conventional techniques. Suitable labels include fluorophores, chromophores, radioactive atoms (particularly $^{32}P$ and $^{125}I$), electron-dense reagents, enzymes, and ligands having specific binding partners. Enzymes are typically detected by their activity. For example, horseradish peroxidase is usually detected by its ability to convert 3,3,5,5'-tetramethylbenzidine (TMB) to a blue pigment, quantifiable with a spectrophotometer. "Specific binding partner" refers to a protein capable of binding a ligand molecule with high specificity, as for example in the case of an antigen and a monoclonal antibody specific therefor. Other specific binding partners include biotin and avidin or streptavidin, IgG and protein A, and the numerous receptor-ligand couples known in the art. It should be understood that the above description is not meant to categorize the various labels into distinct classes, as the same label may serve in several different modes. For example, $^{125}I$ may serve as a radioactive label or as an electron-dense reagent. HRP may serve as enzyme or as antigen for a mAb. Further, one may combine various labels for desired effect. For example, mAbs and avidin also require labels in the practice of this invention: thus, one might label a mAb with biotin, and detect its presence with avidin labeled with $^{125}I$, or with an anti-biotin mAb labeled with HRP. Other permutations and possibilities are readily apparent to those of ordinary skill in the art, and are considered as equivalents within the scope of the instant invention.

IV. Compositions Including Immunosuppressive Agents

A composition of the current invention comprises two components which together are therapeutically effective in preventing or treating graft rejection, GVHD, or rheumatoid arthritis. The two components are: (1) a molecule that binds to the B7-1 antigen such as MAb B7-24; and (2) an immunosuppressive agent. Molecules that bind to the B7-1 antigen include CD28, CTLA4, CTLA4Ig and anti-B7 antibodies as described in Section III above.

The anti B7-1 antibodies of the invention (or other molecules that bind to the B7-1 antigen) are given in combination with one or more immunosuppressive agents. Immunosuppressive agents are agents that block or inhibit the activation or proliferation of T cells. The immunosuppressive agents according to this invention include cyclosporin A (CsA), corticosteroids (methotrexate, prednisolone, dexamethasone), FK506, and rapamycin. Preferably the immunosuppressive agent is cyclosporin A, FK506 or a corticosteroid, most preferably cyclosporin A.

VI. Formulations and Methods of Administration

The antibodies and compositions of this invention are administered at a concentration that is therapeutically effective to halt transplant rejection, or prevent or treat (1) GVHD or rheumatoid arthritis, or (2) antibody-mediated diseases such as allergies, SLE, PBC and ITP. To accomplish this goal, the antibodies or compositions may be formulated using a variety of acceptable excipients known in the art. Typically, the antibodies or compositions are administered by injection, either intravenously or intraperitoneally. Methods to accomplish this administration are known to those of ordinary skill in the art. It may also be possible to obtain compositions which may be topically or orally administered, or which may be capable of transmission across mucous membranes.

Before administration to patients, formulants may be added to the antibodies. A liquid formulation is preferred. For example, these formulants may include oils, polymers, vitamins, carbohydrates, amino acids, salts, buffers, albumin, surfactants, or bulking agents. Preferably carbohydrates include sugar or sugar alcohols such as mono, di, or polysaccharides, or water soluble glucans. The saccharides or glucans may include fructose, dextrose, lactose, glucose, mannose, sorbose, xylose, maltose, sucrose, dextran, pullulan, dextrin, alpha and beta cyclodextrin, soluble starch, hydroxethyl starch and carboxymethylcellulose, or mixtures thereof. Sucrose is most preferred. "Sugar alcohol" is defined as a $C_4$ to $C_8$ hydrocarbon having an —OH group and includes galactitol, inositol, mannitol, xylitol, sorbitol, glycerol, and arabitol. Mannitol is most preferred. These sugars or sugar alcohols mentioned above may be used individually or in combination. There is no fixed limit to amount used as long as the sugar or sugar alcohol is soluble in the aqueous preparation. Preferably, the sugar or sugar alcohol concentration is between 1.0 w/v % and 7.0 w/v%, more preferable between 2.0 and 6.0 w/v %. Preferably amino acids include levorotary (L) forms of carnitine, arginine, and betaine; however, other amino acids may be added. Preferred polymers include polyvinylpyrrolidone (PVP) with an average molecular weight between 2,000 and 3,000, or polyethylene glycol (PEG) with an average molecular weight between 3,000 and 5,000. It is also preferred to use a buffer in the composition to minimize pH changes in the solution before lyophilization or after reconstitution. Most any physiological buffer may be used, but citrate, phosphate, succinate, and glutamate buffers or mixtures thereof are preferred. Most preferred is a citrate buffer. Preferably, the concentration is from 0.01 to 0.3 molar. Surfactants that can be added to the formulation are shown in EP Nos. 270,799 and 268,110.

Additionally, antibodies can be chemically modified by covalent conjugation to a polymer to increase their circulating half-life, for example. Preferred polymers, and methods to attach them to peptides, are shown in U.S. Pat. Nos. 4,766,106; 4,179,337; 4,495,285; and 4,609,546 which are all hereby incorporated by reference in their entireties. Preferred polymers are polyoxyethylated polyols and polyethylene glycol (PEG). PEG is soluble in water at room temperature and has the general formula: R(O—$CH_2$—$CH_2$)$_n$O—R where R can be hydrogen, or a protective group such as an alkyl or alkanol group. Preferably, the protective group has between 1 and 8 carbons, more preferably it is methyl. The symbol n is a positive integer, preferably between 1 and 1,000, more preferably between 2 and 500. The PEG has a preferred average molecular weight between 1000 and 40,000, more preferably between 2000 and 20,000, most preferably between 3,000 and 12,000. Preferably, PEG has at least one hydroxy group, more preferably it is a terminal hydroxy group. It is this hydroxy group which is preferably activated to react with a free amino group on the inhibitor. However, it will be understood that the type and amount of the reactive groups may be varied to achieve a covalently conjugated PEG/antibody of the present invention.

Water soluble polyoxyethylated polyols are also useful in the present invention. They include polyoxyethylated sorbitol, polyoxyethylated glucose, polyoxyethylated glycerol (POG), etc. POG is preferred. One reason is because the glycerol backbone of polyoxyethylated glycerol is the same backbone occurring naturally in, for example, animals and humans in mono-, di-, triglycerides. Therefore, this branching would not necessarily be seen as a foreign agent in the body. The POG has a preferred molecular weight in the same range as PEG. The structure for POG is shown in Knauf et al., *J. Bio. Chem.*, 263, 15064–15070 (1988), and a discussion of POG/IL-2 conjugates is found in U.S. Pat. No. 4,766,106, both of which are hereby incorporated by reference in their entireties.

Another drug delivery system for increasing circulatory half-life is the liposome. Methods of preparing liposome delivery systems are discussed in Gabizon et al., *Cancer Research*, 42, 4734 (1982); Cafiso, *Biochem. Biophys. Acta*, 649, 129 (1981); and Szoka, *Ann. Rev. Biophys. Eng.*, 9, 467 (1980). Other drug delivery systems are known in the art and are described in, e.g., Poznansky et al., DRUG DELIVERY SYSTEMS (R. L. Juliano, ed., Oxford, N.Y. 1980), pp. 253–315; M. L. Poznansky, *Pharm. Revs.*, 36, 277 (1984).

After the liquid pharmaceutical composition is prepared, it is preferably lyophilized to prevent degradation and to preserve sterility. Methods for lyophilizing liquid compositions are known to those of ordinary skill in the art. Just prior to use, the composition may be reconstituted with a sterile diluent (Ringer's solution, distilled water, or sterile saline, for example) which may include additional ingredients. Upon reconstitution, the composition is preferably administered to subjects using those methods that are known to those skilled in the art.

The anti-B7 antibodies of the present are preferably used to prevent or treat transplant rejection, GVHD or rheumatoid arthritis. The preferred route of administration for these antibodies is parenteral. In parenteral administration, the compositions of this invention will be formulated in a unit dosage injectable form such as a solution, suspension or emulsion, in association with a pharmaceutically-acceptable parenteral vehicle. Such vehicles are inherently nontoxic and nontherapeutic. Examples of such vehicles are saline, Ringer's solution, dextrose solution, and Hanks' solution. Nonaqueous vehicles such as fixed oils and ethyl oleate may also be used. A preferred vehicle is 5% dextrose in saline. The vehicle may contain minor amounts of additives such as substances that enhance isotonicity and chemical stability, including buffers and preservatives.

The dosage and mode of administration will depend on the individual. Generally, the compositions are administered so that antibodies are given at a dose between 1 µg/kg and 20 mg/kg, more preferably between 20 µg/kg and 10 mg/kg, most preferably between 1 and 7 mg/kg. Preferably, it is given as a bolus dose, to increase circulating levels by 10–20 fold and for 4–6 hours after the bolus dose. Continuous infusion may also be used after the bolus dose. If so, the antibodies may be infused at a dose between 5 and 20 µg/kg/minute, more preferably between 7 and 15 µg/kg/minute.

The following examples illustrate, but in no way are intended to limit, the present invention.

Materials and Methods

Iscove's modification of Dulbecco's Eagle medium (IMDM) and foetal bovine serum were obtained from JR Biosciences (Lenexa, Kans.); penicillin and streptomycin were obtained from Irvine (Santa Ana, Calif.); and polyethylene glycol (mol. wt. 1500) was obtained from Boehringer Mannheim (Indianapolis, Ind.).

Culture Media

SP2/0 murine myeloma cells, hybridoma cells, purified T cells, EBV-transformed B cells and cell lines were cultured in IMDM supplemented with streptomycin (200 µg/ml), penicillin (200 U/ml) and 10% heat inactivated foetal bovine serum (complete IMDM). The Sf9 insect cells were cultured in shaker flasks agitated (125– 150 rpm) in medium described by Maiorella et al. (1989) supplemented with 0.5% foetal bovine serum. 3T6-FcγRII cells were cultured in medium consisting of 50% Dulbecco's modified Eagle's medium and 50% HAM-FLO medium, supplemented with aminopterin (0.2 µg./ml), thymidine (5 µg/ml), xanthine (10 µg/ml), hypoxanthine (15 µg/ml), mycophenolic acid (20 µg/ml) deoxycytidine (2.3 µg/ml), and 10% heat-inactivated fetal bovine serum (complete DME/HAM-F10). 3T6-FcγRII/B7 cells were cultured in complete DME/HAM-F10 medium containing 400 µg/ml G418 (Gibco).

Cells and Cell Lines.

Peripheral blood mononuclear cells were isolated from heparinized blood (obtained from healthy volunteers) by Ficoll-Hypaque density centrifugation. T cells were enriched by depleting monocytes and B cells using Lymphokwik (Lambda, Calif.) (1 λ). The EBV-transformed B cell line ARC and the P815 cell line, a NK-resistant murine mastocytoma cell line that expresses FcγRII and FcγRIII [Ra et al., i Nature, 341, 752 (1989)], were obtained from the ATCC (Rockville, Md.). 3T6-FcγRII, the mouse fibroblast cell line expressing CD32, the human FcγRII high responder allele, as described by Warmerdam, P.A.M. et al., *J. Exp. Med.*, 172, 19 (1990), was kindly provided by Dr. J. van de Winkel (University Hospital, Utrecht, The Netherlands). The mutant mouse thymoma EL-4 subclone EL4B5 was a gift of Dr. R. H. Zubler, Hôpital Cantonal Universitaire, Geneva. Mouse 3T6 transfectant cells expressing hybrid molecules of the HR (high responder) allelic form of human FcγRIIa were a gift of Dr. P. A. M. Warmerdam, Department of Experimental Immunology, University Hospital Utrecht, Utrecht, The Netherlands. Warmerdam et al., *J. Immunol.*, 147, 1338 (1991). Both cell lines were cultured in Iscove's Modified Dulbecco's Medium (IMDM), supplemented with gentamycin (80 µg/ml) and 10% heat-inactivated fetal calf serum (FCS) (Hyclone, Logan, Utah). To avoid possible loss of B cell activating capacity, every 4 to 8 weeks a new batch of EL4B5 cells was thawed. The cell lines were periodically tested for mycoplasma contamination by the use of a $^3$H-labelled DNA probe for mycoplasma ribosomal RNA (GenProbe, San Diego, Calif.) and were free of mycoplasma during the course of the experiments.

Human B Lymphocytes.

B lymphocytes were isolated from tonsils obtained from children undergoing tonsillectomies, essentially as described in De Groot et al., *Lymphokine Research*, 9, 321 (1990). Briefly, the tissue was dispersed with scalpel blades, phagocytic and NK cells were depleted by treatment with 5 mM L-leucine methyl ester and T cells were removed by one cycle of rosetting with sheep erythrocytes (SRBC) treated with 2-aminoethyl isothiouronium bromide. The purity of the resulting B lymphocyte preparations was checked by indirect immunofluorescent labelling with anti-(CD20) mAb B1 (Coulter Clone, Hialeah, FA) or anti-(CD3) mAb OKT3 (Ortho, Raritan, N.J.) and a FITC-conjugated F(ab')$_2$ fragment of rabbit anti-(mouse Ig) (Zymed, San Francisco, Calif.), and FACS analysis. The B cell preparations contained (mean ± SD of 6 isolations): 95±4% CD20-positive cells and 2±1% CD3-positive cells.

Antibodies.

Anti-(human B7) monoclonal antibody BB-1 (Yokochi et al., 1982) was obtained from Dr. E. A. Clark (University of Washington, Seattle, Wash.) and was used as purified antibody. Anti-(human CD26) monoclonal antibody Ta-1 and anti-(CD20) monoclonal antibody B1 were obtained from Coulter (Hialeah, Fla.). Anti-(CD3) monoclonal antibody OKT3 was obtained from Ortho (Raritan, N.J.), and the anti-(LeuM3) monoclonal antibody was obtained from Becton-Dickinson (San Jose, Calif.). Anti-(IgM) antibodies coupled to beads (Immunobeads) were obtained from Bio-Rad (Richmond, Calif.).

Anti-B7 Mab B7-24 (IgG2a, κ) was obtained as described in Section II above, and used as a purified antibody. Anti-CD3 Mab CLB-T3/4.1 (IgG1, κ) was used as diluted tissue culture supernatant and was kindly supplied by Dr. L. Aarden (Central Laboratory of the Red Cross Blood Transfusion Service, Amsterdam, The Netherlands). Anti-CD3 Mab UCHT1 (IgG, κ) was used as purified antibody and as a gift of Dr. P. Beverley (Imperial Research Cancer Fund, London, UK). Anti-CD72 Mab WL225 (IgG2a, x) was used as purified antibody and was a gift of Dr. K. Thielemans (Vrije Universiteit Brussel, Belgium). The anti-ICAM-1 Mab 84H10 was used as diluted ascites fluid. Control antibodies were: anti-(β-glucocerebrosidase) mAb 8E4 (IgG1), Barneveld et al., *Eur. J. Biochem.*, 134, 585 (1983), and myeloma immunoglobulins MOPC-21 (IgG1) and MOPC-141 (IgG2b) (Sigma, St. Louis, Mo.). All mAb were used as purified antibody preparations.

The monoclonal antibodies of the present invention can be labeled, by standard methods, using a number of reporter moieties, including the following: fluorescent labels (fluorescein (FITC), R-phycoerythrin, rhodamine (TMRITC), rhodamine 600 (XRITC), "TEXAS RED," and the like, commonly avidin linked); radioactive moieties ($^{125}$I and the like); light-emitting (luciferase and the like); enzymatic (horseradish peroxidase, alkaline phosphatase, glucose oxidase, β-galactosidase, and the like). Further, reporter antibodies (antibodies which have binding specificity for the monoclonal antibodies of the present invention, e.g., goat anti-mouse IgG) can also use the above-listed labelling moieties.

Enzymes and Oligonucleotides.

*E. coli* DNA polymerase I (Klenow fragment) was obtained from Boehringer Mannheim Biochemicals (BMB) (Indianapolis, Ind.). T4 DNA ligase and T4 DNA polymerase were obtained from New England Biolabs (Beverly, Mass.); Nitrocellulose filters are obtained from Schleicher and Schuell (Keene, N.H.). Synthetic oligonucleotide linkers and primers were prepared using commercially available automated oligonucleotide synthesizers. Alternatively, custom designed synthetic oligonucleotides may be purchased, for example, from Synthetic Genetics (San Diego, Calif.). cDNA synthesis kit and random priming labeling kits are obtained from Boehringer-Mannheim Biochemical (BMB, Indianapolis, Ind.). Oligonucleotide sequences encoding peptides can be either synthesized as described above. Alternatively, peptides can be synthesized directly by standard in vitro techniques (Applied Biosystems, Foster City Calif.).

Common manipulations involved in polyclonal and monoclonal antibody work, including antibody purification, were performed by standard procedures (Harlow, et al.).

Fluorescent Cell Staining (FACS) Assay.

Cells ($10^6$/sample) were incubated in 10 µl primary antibody (10 µl/ml in PBS-BSA or HBSS (Hanks' Balanced Salt Solution, Gibco/BRL) supplemented with 1% BSA and 0.05% sodium azide) for 20 minutes at 4° C. After 3 washes with PBS-BSA or HBSS-BSA, the cells were incubated in 100 µl FITC-labeled $F_{ab'2}$ fragments of goat anti-(mouse IgG) antibodies (Jackson, West Grove, Pa.) for 20 minutes at 4° C. After 3 washes with PBS-BSA or HBSS-BSA and 1 wash with PBS, the cells were resuspended in 0.5 ml PBS. Analyses were performed with a FACSSCAN V (Becton Dickinson, San Jose, Calif.).

B7-Mediated T Cell Proliferation Assay.

Purified T cells were cultured with 3T6 fibroblasts transfected with the FcγRIIa high responder allele and the B7-1 molecule [de Boer et al., *Eur. J. Immunol.*, 22, 3071–3075 (1992)]. Proliferation was measured by $^3$H-thymidine incorporation. Briefly, $4 \times 10^4$ T cells were cultured with $10^4$ irradiated (2500 rads) 3T6-FcγRII/B7-1 cells in 96-well flat-bottom tissue culture plates in 200 µl/well complete IMDM with or without anti-CD3 Mab CLB-T3/4.1. During the last 16 hours of a 72 hour culture period, the cells were pulsed with 1 µCi/well $^3$H-thymidine. Proliferation of T cells is expressed as the mean cpm of triplicate wells.

Cytotoxic T Cell Assay.

Purified T cells were cultured with 3T6 fibroblasts transfected with the FcγRIIa high responder allele and the B7-1 molecule. Briefly, $10^6$ T cells were cultured with $0.2 \times 10^6$ irradiated (2500 rads) 3T6-FcγRII/B7-1 cells in 24-well flat-bottom tissue culture plates in 1 ml/well complete IMDM in the presence of anti-CD3 Mab UCHT1 for 3–4 days. The cytotoxic activity of the lymphocytes was analyzed in an anti-CD3-redirected cytotoxicity assay as described below.

Mixed Lymphocyte Culture (MLC) Assay.

Proliferation of purified T cells was measured in mixed lymphocyte cultures (MLC) using the EBV-transformed B cell line ARC as stimulator cells. $5 \times 10^4$ T cells were cultured with $5 \times 10^4$ irradiated (5000 rads) stimulator cells in 96-well round-bottom tissue culture plates (Corning) in 200 µl/well complete IMDM medium. During the last 16 hours of a 72 hour culture period, the cells were pulsed with 1 µCi/well $^3$H-thymidine. Proliferation of T cells is expressed as the mean cpm of triplicate wells. For secondary MLCs, cells were stimulated as described above for primary MLC. The T cell blasts for secondary MLC were generated in 5- to 7-day primary MLC, with subsequent culture in the absence of the stimulator cells for 2–4 days. The cytotoxic activity of T cells generated in primary or secondary MLC was analyzed in an anti-CD3-redirected cytotoxicity assay using the mouse P815 cells as described below. Alternatively, the EBV-transformed B cells used to induce the CTL activity served as target cells.

Cytotoxicity Assay.

CTL activity was determined in a 4 hour target cell lysis assay using P815 murine mastocytoma cells or ARC EBV-transformed B cells as targets. In the case of the P815 target cells the CTLs were bridged non-specifically to the target cells using the anti-CD3 Mab OKT3 at 2 µg/ml. When the ARC cells were used as target cells, only the alloantigen-specific CTLs participate in the killing process. $10^6$ target cells were incubated with 200 µCi of $^{51}$Cr-sodium chromate (Amersham International) for one hour and subsequently washed. The CTL assays were performed in 96-well V-bottom microtiter plates using 5000 $^{51}$Cr-labelled target cells with different amounts of effector cells in a total volume of 200 µl/well. Four wells were filled with $5 \times 10^3$ target cells in 200 µl medium alone, and four wells with $5 \times 10^3$ target cells in 100 µl medium and 100 µl saponin (for evaluation of spontaneous and maximal release, respectively). In the case of the P815 cells, three wells were filled with effector cells and target cells in the absence of anti-CD3 Mab (to determine the background experimental lysis). Three other wells also contained the anti-CD3 Mab at 2 µg/ml in order to determine the total lysis in the presence of anti-CD3. The plates were centrifuged for 10 minutes at 200×g and incubated for four hours at 379° C. Afterwards, 100 µl of the supernatant of each well was counted in a gamma counter. Results are expressed as percentage of anti-CD3-dependent specific release with the P815 target cells, or as a percentage of alloantigen-specific release with the ARC target cells.

Flow Cytofluorometric Assay.

ARC cells ($10^6$ cells/sample) were incubated in 100 µl primary antibody (10 µg/ml in PBS-BSA or Hanks' balanced salt solution (HBSS) supplemented with 1% BSA and 0.05% sodium azide) for 20 min. at 4° C. After 3 washes with PBS-BSA or HBSS-BSA, the cells were incubated in 100 µl FITC-labeled F(ab')$_2$ fragments of goat anti-(mouse IgG) antibodies (Jackson, West Grove, Pa.) for 20 min. at 4° C. After 3 washes with PBS-BSA or HBSS-BSA and 1 wash with PBS, the cells were resuspended in 0.5 ml PBS. Analyses were performed with a FACSCAN V (Becton Dickinson, San Jose, Calif.).

EXAMPLE 1

PCR Cloning of B7

RNA was isolated from a population of EBV-transformed human spleen cells essentially as described by Chirgwin et al. (1979). In brief, the cells were washed twice with phosphate buffered saline (PBS) and lysed in 5M guanidinium thiocyanate in the presence of 0.7M 2-mercaptoethanol. The cell lysate was layered on a discontinuous CsCl gradient (Chirgwin et al.) and centrifuged for 16 hours at 26,000 rpm in a Beckman SW28 rotor. The RNA was recovered by dissolving the pellet in DEPC-treated H$_2$O. The RNA was precipitated with ethanol once, resuspended in DEPC treated H$_2$O, and stored at –70° C.

Total RNA (10 µg/reaction) was converted to cDNA using random hexamer priming in 50 µl reaction buffer containing 500 units LMV-RT (Bethesda Research Laboratories, Bethesda, Md.), 5 µM random hexamers (Pharmacia, Piscataway, N.J.), 1 mM DTT, dNTP mix (0.5 mM each), 10 mM Tris-HCL pH 8.3, 50 mM KC1, 2.5 MM MgCl$_2$ and 0.1 mg/ml BSA (bovine serum albumin). After incubation at 37° C. for 1 hour, the samples were boiled for 3 min and stored at –70° C. The DNA encoding the B7-1 molecule was generated by PCR using primers which contained sequences having homology to the B7 sequence, where the primers also encoded restriction sites useful for cloning (FIG. 2). These primers were based on the published cDNA coding sequence for B7-1 (Freeman et al., 1989). All primers start with a C-G clamp at the 5' end followed by a restriction site for cloning (shown in bold, FIG. 2). The underlined sequences in the backward primers, for the cloning of the soluble form of B7-1, represents an epitope recognized by a monoclonal antibody used for affinity purification. The numbers in brackets represent the location of the primers relative to the published cDNA for B7-1.

For PCR amplification, 1 µl of CDNA was mixed 1 µl (10 picomoles) of a forward primer, 1 µl (10 picomoles) of a backward primer, and 47 µl of PCR mix. The PCR mix consisted of 1.25 units Taq polymerase (Perkin-Elmer/Cetus, Norwalk, CT), dNTP mix (0.2 mM each), 10 mM Tris-cHL pH 8.3, 50 mM KCl, 2.5 MM $MgCl_2$ and 0.1 mg/ml BSA. The 50 µl of PCR mixture was overlaid with 70 µl mineral oil and subjected to 25 cycles of amplification in a Perkin-Elmer/Cetus thermocycler (denaturation at 95° C. for 30 sec, primer annealing at 55° C. for 30 sec and extension at 72° C. for 1.5 min). PCR products were obtained after 25 amplification cycles.

The amplification products were digested with BglII and KpnI (FIG. 1B) and isolated by size-fractionation. Before expression in baculovirus, the DNA sequence of each fragment was confirmed by sequencing analysis to prevent the introduction of PCR-induced mutations. The baculovirus transfer vector pAcC8 was also digested with BglII and KpnI (FIG. 1B).

The amplified fragments were ligated to the linear pAcC8 vector (ratio of insert to vector was 3:1). The ligation products were transformed into bacterial strain DH5α (Gibco/BRL, Gaithersburg Md.) and recombinant pAcC8 vectors were selected on the basis of ampicillin resistance. Recombinant plasmids were isolated from bacterial clones (Maniatis et al.; Ausubel, et al.) and the presence of the insert of interest verified using polymerase chain reactions (see above). Large scale plasmid preparation was performed by standard procedures (Ausubel et al.; Maniatis et al.; Sambrook et al.).

EXAMPLE 2

Baculovirus Expression of Human B7

Sequences encoding human B7 were recombined into the *Autographa californica* baculovirus (ACNPV) using the transfer vectors pAcB7 (encoding the full-length B7-1 molecule) and pCcB7-ED/Glu (encoding the cellular domain of the B7 molecule).

The plasmids were cotransfected with wild-type baculoviral DNA (2–10 pfu) (AcNPV; Summers et al.) into SF9 (*Spodoptera frugiperda*) cells at a density of $10^6$ cells/ml (Summers et al.). Recombinant baculovirus-infected Sf9 cells were identified and clonally purified (Summers et al.).

For cell surface expression of recombinant proteins the cells were harvested after 48 hours of culture; for the production of secreted recombinant proteins, the cells were harvested after 72 hours of culture.

EXAMPLE 3

Sf9 Cell ELISA

Sf9 insect cells infected with recombinant virus were cultured for 48 hours in 24-well plates. After removal of the tissue culture medium the plates were incubated for 45 min at room temperature (RT) with 0.25 ml of antibody in PBS with 1% BSA (PBS-BSA). After three washed with PBS-BSA, the plates were incubated for 35 min at RT with 250 µl of a 1/250 dilution of goat anti-(mouse total Ig) immunoglobulins conjugated to horseradish peroxidase (Zymed, South San Francisco, Calif.) in PBS-BSA. Unbound peroxidase activity was removed by washing five times with PBS-BSA. Bound peroxidase activity was revealed by the addition of an assay mixture prepared by diluting 0.5 ml of 2 mg/ml 3,3', 5,5'-tetramethylbenzidine in ethanol to 10 ml with 10 mM Na acetate, 10 mM EDTA buffer (pH 5.0) and adding 0.03% (v/v) $H_2O_2$. The reaction was stopped after 10 min by adding 100 µl of 1M $H_2SO_4$.

The above-described ELISA assays performed on live Sf9 cells gave the following results. FIG. 3 presents the data for Sf9 cells infected with pAcB7 and pAcCD26 which were cultured for 48 hours in 24-well plates. The antibodies used in the ELISA were: BB-1 anti-(B7) (open bars), Ta-1, anti-(CD26) (hatched bars) and no primary antibody (gray bars).

EXAMPLE 4

Fluorescent Cell Staining

A. Fluorescent Cell Staining

Cells ($10^6$/sample) were incubated in 10 µl primary antibody (10 µg/ml in PBS-BSA or HBSS (Hanks' Balanced Salt Solution, Gibco/BRL) supplemented with 1% BSA and 0.05% sodium azide) for 20 min at 40° C. After 3 washes with PBS-BSA or HBSS-BSA, the cells were incubated in 100 µl FITC-labeled Fab'2 fragments of goat anti-(mouse IgG)antibodies (Jackson, West Grove, Pa.) for 20 min at 4° C. After 3 washes with PBS-BSA or HBSS-BSA and 1 wash with PBS, the cells were resuspended in 0.5 ml PBS. Analyses were performed with a FACSSCAN V (Becton Dickinson, San Jose, Calif.).

General protocols for flow cytometric analysis and clinical data analysis for flow cytometry are detailed in Keren et al. and Coon et al. General blood cell counting techniques and DNA quantitation are described by Powers, Keren et al. and Coon et al.

The data for fluorescent cell staining of ARC EBV transformed B cells is presented in FIG. 4. In FIG. 4; the results for staining at 1:100 dilution of serum from a mouse immunized with B7 expressing Sf9 cells (solid line) or a 1:100 dilution of normal mouse serum (dotted line) are shown.

B. Soluble Antigen Competition Assays

ARC EBV-transformed B cells were stained with an anti-(B7-1) monoclonal antibody in the presence and absence of soluble B7-1. The antibodies and the soluble B7 or controls were preincubated at RT for 20 min before addition to the ARC cells.

FIG. 6A shows the results of staining with B7-24 (dotted line) or secondary antibody only (solid line). FIG. 6B shows the results of staining with B7-24 alone (dotted line) or B7-24 preincubated with soluble B7 (solid line).

EXAMPLE 5

Host Animal Immunization

Female BALB/c mice were injected intraperitoneally at day 0 and day 14 with $5 \times 10^6$ Sf9 cells infected with AcB7 virus or AcCd3 virus (control virus). At day 21, 100 µl of serum was obtained to test for the presence of specific antibodies. After a rest period of at least two weeks, the mice received a final injection with $5 \times 10^6$ cells infected with AcB7 virus. Three days after this last injection, the spleen cells were used for cell fusion.

EXAMPLE 6

Generation of Hybridoma Clones

Splenocytes from immunized BALB/c mice were fused with SP2/0 murine myeloma cells at a ratio of 10:1 using 50% polyethylene glycol as previously described by de Boer et al. (1988). The fused cells were resuspended in complete IMDM medium supplemented with hypoxanthine (0.1 mM), aminopterin (0.01 mM), thymidine (0.016 mM) and 0.5 ng/ml hIL-6 (Genzyme, Cambridge, Mass.). The fused cells were then distributed between the wells of 96-well tissue culture plates, so that each well contained 1 growing hybrid on average.

After 10–14 days the supernatants of the hybridoma populations were screened for specific antibody production. For the screening of specific antibody production by the hybridoma clones, the supernatants of 12 wells were pooled and used for fluorescent cell staining of EBV-transformed B cells as described in Example 4. Subsequently, the supernatants of the positive pools were tested individually. Positive hybridoma cells were cloned three times by limiting dilution in IMDM/FBS containing 0.5 ng/ml hIL-6. The results of the analysis are presented in Table 1.

TABLE 1

Summary of Fusion Data for the Generation of Monoclonal Antibodies to Human B7

| Fusion: | Anti-B7 |
| --- | --- |
| No. of wells seeded after fusion | 960 |
| No. of wells with hybridoma growth | 312 |
| No. of positive wells | 1 |
| Frequency of positive wells | 0.31 |

In Table 1 only half of the cells obtained after fusion were analyzed. The number of positive well was as determined by FACS analysis described in Example 4. The frequency of positive wells is defined as the number of positive wells divided by the total number of wells with hybridoma growth, multiplied by 100.

EXAMPLE 7

Testing of Tonsillar B Cells

Tonsillar B lymphocytes were isolated from tonsils obtained from children undergoing tonsillectomy as described by deGroot et al. (1990). Briefly, the tissue was dispersed with scalpel blades, phagocytic cells and NK cells were depleted by treatment with 5 mM L-leucine methyl ester and T cells were removed by one cycle of resetting with sheep erythrocytes treated with 2-aminoethyl isothiouronium bromide.

The anti-(B7-1) monoclonal antibody was tested for its ability to bind to tonsillar B cells using the fluorescent cell staining assay described above in Example 4. For fluorescent stain analysis of cultured tonsillar B cells, propidium iodine was used to exclude dead cells.

TABLE 2

Binding of Anti-(B7-1) Monoclonal Antibody B7-24 to Highly Enriched Tonsillar B Cells

| | | % of Positive Cells* | |
| --- | --- | --- | --- |
| Antibody | Specificity | Donor 1 | Donor 2 |
| OKT3 | CD3 | 8.0 | 2.1 |
| B1 | CD20 | 74.0 | 88.0 |
| B7-24 | B7-1 | 12.6 | 16.8 |

In Table 2 the percentage of positive tonsillar cells was measured by flourescent cell staining as described in Example 4.

These data show that 12–17 percent of freshly isolated tonsillar B cells stained positive with anti-(B7) monoclonal antibody B7-24.

EXAMPLE 8

Blocking T Cell Proliferation with Mab B7-24

The role of the B7-1 molecule in T cell activation was studied using the T cell proliferation and MLC assays described above. Proliferation in the absence of B7-24 Fab fragments ranged from 20,000 to 60,000 cpm. FIG. 6 shows that this Mab binds to a functionally important domain of the B7-1 molecule, since it can completely block anti-CD3-induced, B7-1-mediated induction of T cell proliferation. Data shown are the ±S.D. of 4 individual experiments using T cells of different donors.

Figure 7:
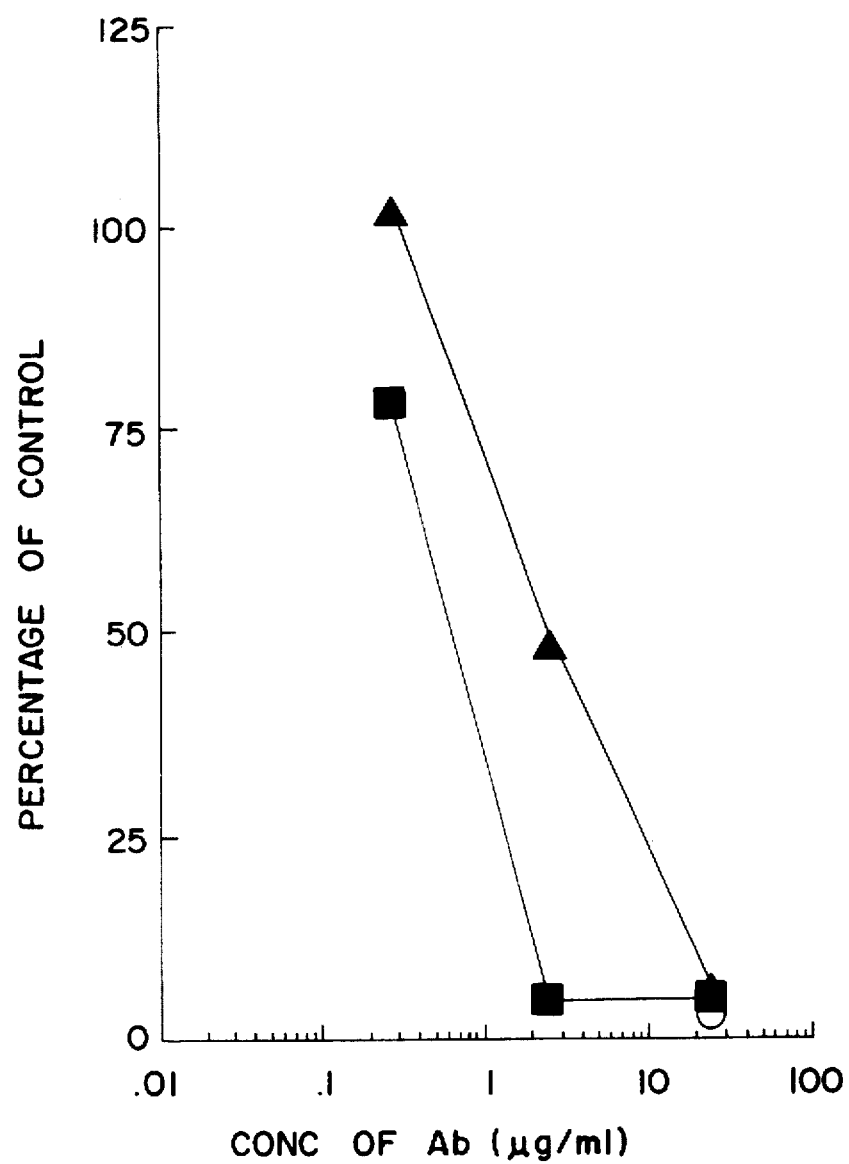
FIG. 7 shows the inhibition of anti-CD3-induced, B7-mediated proliferation of T cells by anti-B7 Mabs B7-24 (squares) or BB-1 (triangles).
Figure 8A:
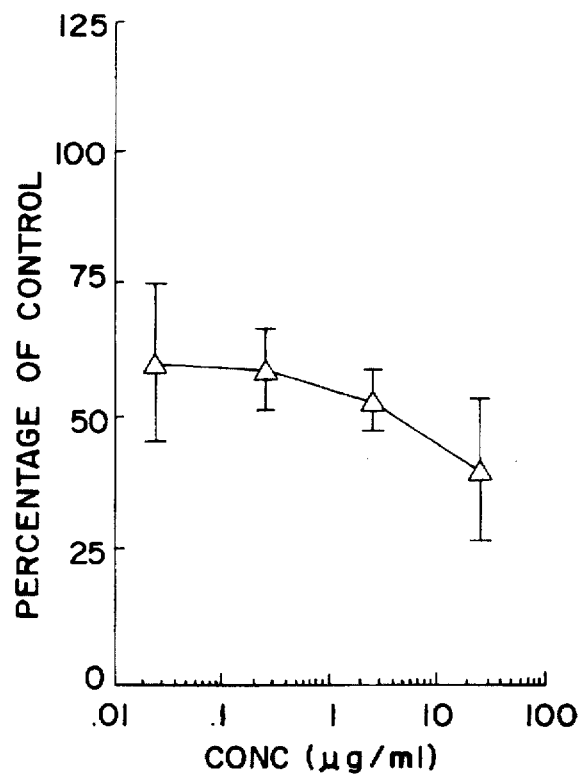
FIG. 8 shows the effect of blocking B7/CD28 interaction using (A) MAb B7-24 or (B) MAb BB-1 during 3-day secondary MLC (open symbols).
Figure 8B:
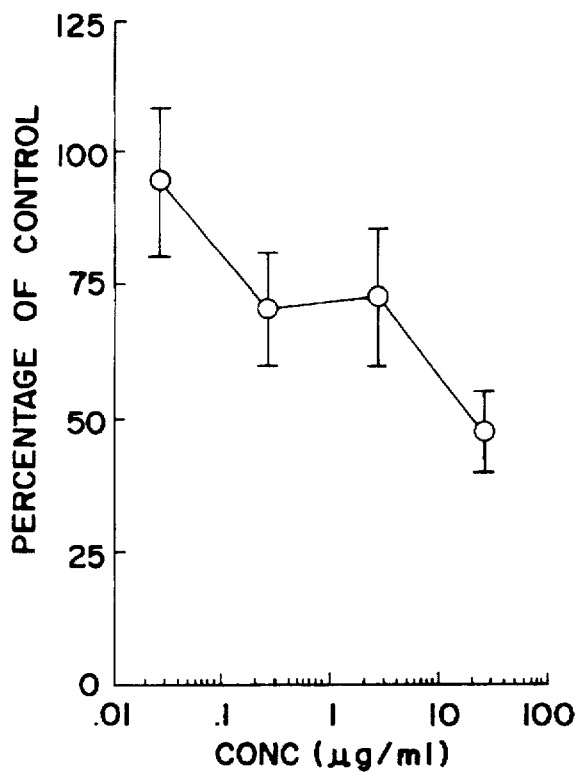

FIG. 7 shows the inhibition of anti-CD3-induced, B7-mediated proliferation of T cells by anti-B7-1 Mabs B7-24 (squares) or BB-1 (triangles). FIG. 8 shows the effect of blocking B7/CD28 interaction during secondary MLC (open symbols). Purified T cells were stimulated with the EBV-transformed B cell line ARC for 3 days in the presence or absence of different concentrations of Mab B7-24 (FIG. 8A) or BB-1 (FIG. 8B). Proliferation in the absence of antibody ranged from 15,000 to 30,000 in primary MLC and from 20,000 to 60,000 in secondary MLC. Data shown are the mean ±S.D. of 4 individual experiments using T cells from different donors.

From this experiment, it is clear that anti-B7 monoclonal antibodies do not completely block primary MLCs. Under the same experimental conditions, however, a Mab to CD3 almost completely blocked the activation of T cells in the primary MLC. Interestingly, when Mab B7-24 was tested for its inhibitory capacity in secondary mixed lymphocyte cultures using pre-activated T cells, it was able to inhibit the activation of T cells.

EXAMPLE 9

Blocking T Cell Proliferation with Cyclosporin A and/or Mab B7-24

Figure 9:
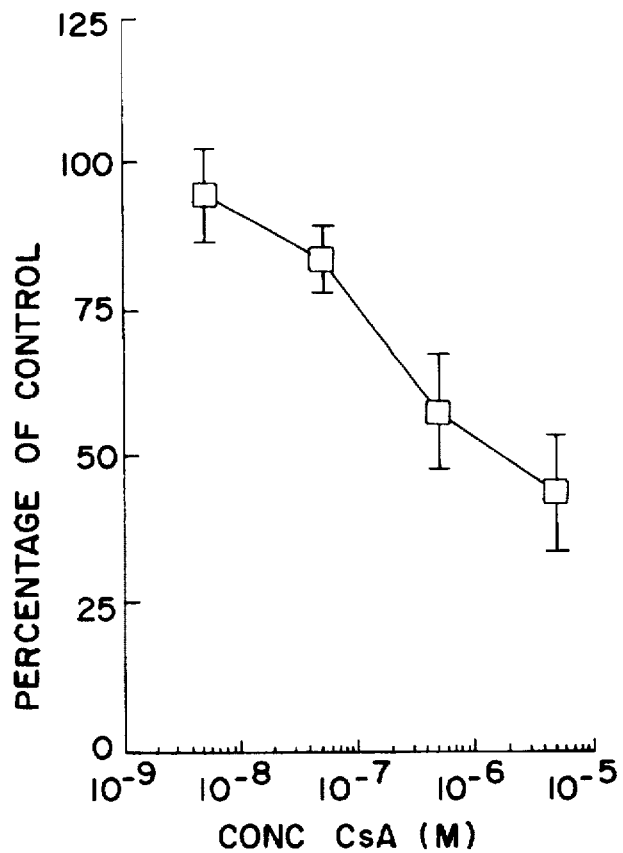
FIG. 9 shows the inhibition of anti-CD3-induced, B7-mediated proliferation of T cells by CsA. Data are the mean ± S.D. of 3 individual experiments using T cells of different donors.

We used the T cell proliferation assay described above to determine whether the costimulation of T cells with B7 is also resistant to inhibition with CsA. FIG. 9 shows that when T cells are induced to proliferate with anti-CD3 Mab, costimulation with B7-1 can be inhibited in a dose-dependent manner by CsA. However, it was not possible to completely block the activation of T cells with CsA concentrations that are not toxic. When CsA was used to block primary MLC (results not shown) or secondary MLC (see Table 3), similar results were obtained. These experiments clearly suggest that B7-1-CD28/CTLA4 mediated T cell proliferation is only partially sensitive to the inhibitory action of CsA. This lack of complete inhibition when T cells are costimulated with B7-1 in vitro could mimic what happens in vivo during graft rejection or acute GVHD despite treatment with CsA.

TABLE 3

CsA and Mab B7-24 Synergy in blocking
T-cell Proliferation in Secondary MLC

| B7-24 (μg/ml) | Cyclosporin A concentration | | | | | | |
|---|---|---|---|---|---|---|---|
| | $6 \times 10^{-6}M$ | $3 \times 10^{-6}M$ | $10^{-6}M$ | $6 \times 10^{-7}M$ | $3 \times 10^{-7}M$ | $10^{-7}M$ | None |
| 2.5 | 971 | 609 | 601 | 790 | 697 | 1,159 | 25,209 |
| 0.25 | 553 | 545 | 601 | 788 | 559 | 882 | 20,753 |
| 0.025 | 897 | 939 | 1,121 | 1,592 | 1,570 | 2,818 | 29,364 |
| None | 12,687 | 15,593 | 23,484 | 24,589 | 27,629 | 33,235 | 62,598 |

In Table 3 entries reflect T-cell proliferation in CPM. Proliferation was measured using the T-cell proliferation assay described above. Data are shown for one of four experiments.

Table 3 shows that CsA alone or mAb B7-24 alone gave a dose-dependent, but incomplete, inhibition of T cell activation. However, when CsA and B7-24 were combined, T cell activation was completely blocked. Interestingly, addition of 0.025 μg/ml B7-24 gave almost the same amount of blocking as 2.5 μg/ml. Furthermore, in the presence of 0.025 μg/ml B7-24, decreasing the CsA concentration 60-fold still resulted in more than 90% inhibition of T cell activation, being more than the maximal inhibition with the highest CsA concentration alone.

This synergy between Mab B7-24 and CsA was specific for the B7/CD28 interaction, since it was not observed using Mabs to either ICAM-1 or CD72 in the same proliferation assay, as shown in Table 4.

TABLE 4

Effects of CsA with B7, ICAM-1
or CD72 Mabs in blocking
T-cell proliferation in a secondary MLC

| Monoclonal Antibody | Concentration (μg/ml) | Cyclosporin A Concentration | | | |
|---|---|---|---|---|---|
| | | $6 \times 10^{-7}M$ | $3 \times 10^{-7}M$ | $10^{-7}M$ | None |
| B7-24 | 2.5 | 3 | 3 | 3 | 40 |
| (α-B7) | 0.25 | 3 | 2 | 3 | 33 |
| | 0.025 | 6 | 6 | 6 | 47 |
| 84H10 | 2.5 | 76 | 84 | 81 | 115 |
| (α-ICAM-1) | 0.25 | 80 | 80 | 76 | 99 |
| | 0.025 | 91 | 99 | 96 | 99 |
| WL225 | 2.5 | 106 | 107 | 89 | 98 |
| (α-CD72) | 0.25 | 108 | 106 | 91 | 100 |
| | 0.025 | 109 | 105 | 93 | 106 |

In Table 4 entries reflect T-cell proliferation expressed as a percentage of control (100%). Proliferation was measured using the T-cell proliferation assay described above.

EXAMPLE 10

Blocking T Cell Proliferation with Mab B7-24 and Other Immunosuppressive Agents

The protocol of Example 9 above is used to show the blocking of T cell proliferation using mab B7-24 in conjunction with other immunosuppressive agents. The proliferation assay protocol in Example 9 is followed substituting (A) FK506, (B) rapamycin, (C) methotrexate, (D) prednisolone, or (E) dexamethasone for CsA.

EXAMPLE 11

Blocking Cytotoxic T Lymphocyte Activity with Cyclosporin A and/or Mab B7-24

Figure 10:
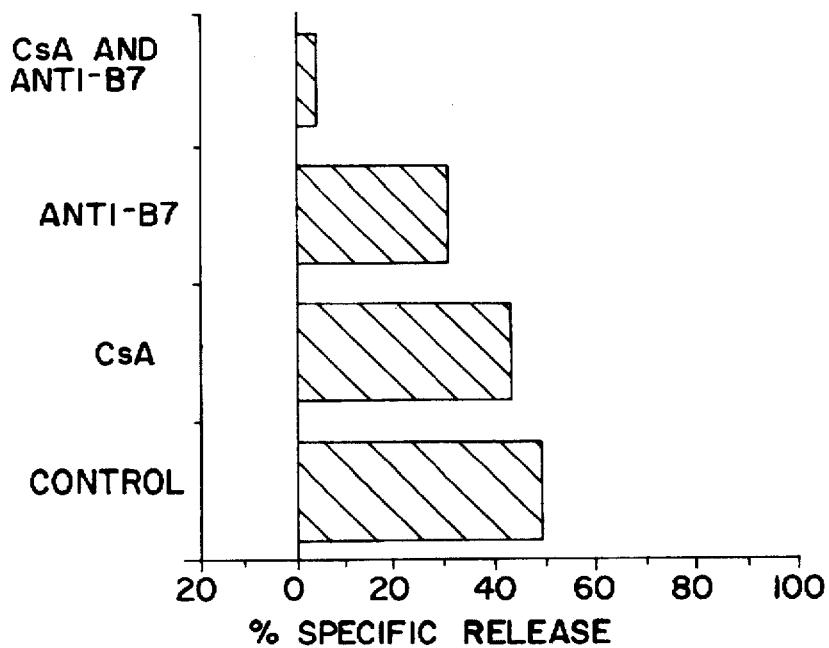
FIG. 10 shows the synergistic effects of the anti-B7-1 Mab B7-24 and CsA in blocking alloantigen-induced CTL activity during secondary MLC. CTL activity of the T cells was analyzed after restimulation for 3 days with the EBV-transformed B cell line ARC in the presence of medium alone; 400 µg/ml CsA; 10 µg/ml Mab B7-24; or 400 µg/ml CsA and 10 µg/ml Mab B7-24.
Figure 12A:
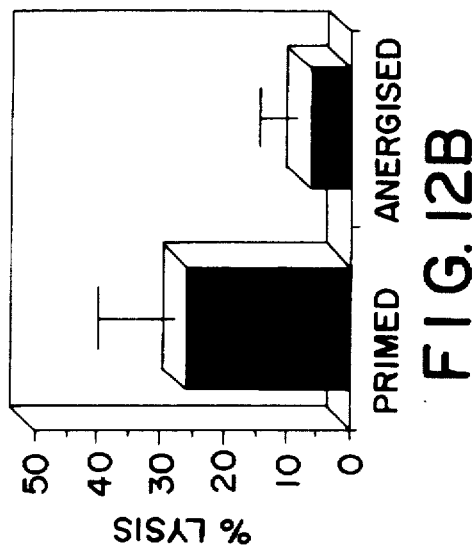
In FIGS. 12A–D. bar graphs illustrate that the combination of CsA and anti-B7-1 during a primary MLR induces persistent alloantigen-unresponsiveness upon restimulation in secondary and tertiary MLR.
Figure 12B:
Figure 12C:
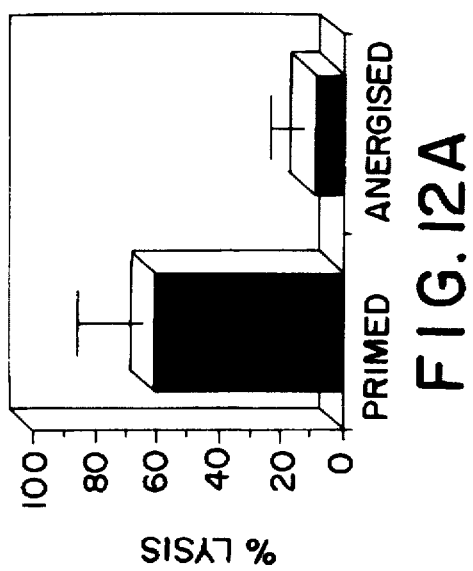
Figure 12D:
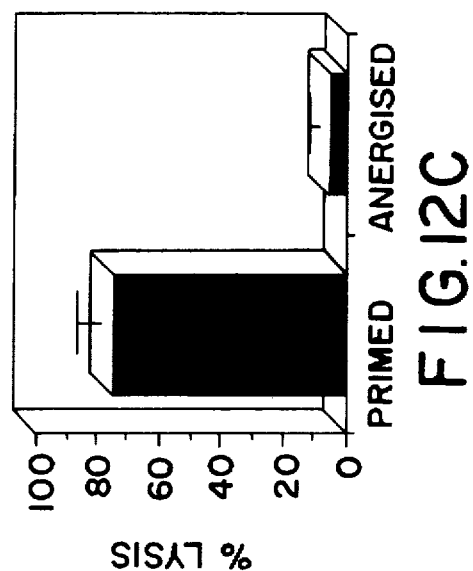

The cytotoxicity assay described above was used to test whether CsA and B7-24 could also cooperate in blocking induction of CTL activity in alloantigen-specific activation of T cells. Purified T cells were stimulated with the EBV-transformed B cell line ARC for 6 days, followed by a 2-day culture period in medium alone. CTL activity of the T cells was analyzed after restimulation for 3 days with the EBV-transformed B cell line ARC in the presence of medium alone; 400 μg/ml CsA; 10 μg/ml Mab B7-24; or 400 μg/ml CsA and 10 μg/ml Mab B7-24, as shown in FIG. 10. T cells activated by the alloantigen in these cultures were efficiently induced to become cytolytic, since about 50% of the ARC target cells could be lysed in the 4 hour assay. This induction of CTL activity in secondary MLC could only be slightly inhibited with 400 ng/ml CsA. Addition of 10 μg/ml Mab B7-24 during the secondary MLC resulted in about 40% inhibition. However, combining CsA and Mab B7-24 resulted in almost complete blockage of the CTL activation.

EXAMPLE 12

Blocking Cytotoxic T Lymphocyte Activity with Mab B7-24 and Other Immunosuppressive Agents The protocol of Example 11 above is used to show the blocking of cytotoxic T lymphocyte activity using Mab B7-24 in conjunction with other immunosuppressive agents. The cytotoxicity assay protocol in Example 11 is followed substituting (A) FK506, (B) rapamycin, (C) methotrexate, (D) prednisolone, or (E) dexamethasone for CsA.

EXAMPLE 13

Combining CsA and Mab B7-24 During Alloantigen-Specific T-Cell Activation

It was investigated whether T cells stimulated in a primary MLC assay (as described above) with the alloantigen in the presence of CsA and Mab B7-24 could respond to secondary antigen stimulation. Purified T cells were stimulated with the EBV-transformed B cell line ARC for 6 days in the presence or absence of 10 μg/ml Mab B7-24 and 400 μg/ml CsA, followed by a 2 day culture period in medium alone. CTL activity of the T cells was analyzed after re-stimulation for 3 days with the EBV-transformed B cell line ARC. The data in Table 5 is that of a representative experiment, showing that 6-day exposure to the alloantigen in the presence of both CsA and Mab B7-24, but not in the presence of CsA or Mab B7-24 alone, resulted in total unresponsiveness for subsequent challenge with the alloantigen in secondary MLC. This unresponsiveness was not due to lack of viability of the cells after the primary MLC, since in a control experiment the cell population could still be induced to become cytotoxic after stimulation with immobilized anti-CD3 Mab or cells expressing a non-related alloantigen (results not shown).

TABLE 5

Alloantigen-Specific T Cell Tolerance
Induced by the combination of CsA and B7-24

| Additions of Culture Medium | (% specific release) | |
|---|---|---|
| During Primary MLC | P815 | ARC |
| None | 80 | 49 |
| B7-24 (10 µg/ml) | 78 | 24 |
| CsA (400 ng/ml) | 76 | 37 |
| B7-24 & CsA | 0 | 0 |

In Table 5 CTL activity of purified T cells in secondary MLC with ARC cells as stimulator cells, after primary MLC as described above. CTL activity measured in T cell cytotoxicity assay as described above.

EXAMPLE 14

Combining Mab B7-24 and an Immunosuppressive Agent During Alloantigen-Specific T-Cell Activation The protocol of Example 13 above is used to show the ability of Mab B7-24 in conjunction with other immunosuppressive agents to block secondary antigen stimulation. The CTL assay protocol in Example 13 is followed substituting (A) FK506, (B) rapamycin, (C) methotrexate, (D) prednisolone, or (E) dexamethasone for CsA.

Deposition of Cultures

The hybridoma used in the above examples was deposited in and accepted by the American Type Culture Collection (ATCC), 12301 Parklawn Drive, Rockville, Md., 20852 USA, under the terms of the Budapest Treaty. This deposition does not indicate that these hybridomas are necessary to practice the invention described above or claimed below.

TABLE 6

| Hybridoma | Deposit Date | Accession No. |
|---|---|---|
| B7-24-EIG4 (i.e., B7-24) | May 6, 1993 | HB 11341 |

Monoclonal antibody B7-24 binds to a different antigenic epitope on the B7-1 molecule than the BB-1 monoclonal antibody and the CTLA-4 Ig fusion protein: B7-24 does not bind to B7-2, whereas CTLA-4 Ig does; B7-24 and CTLA-4 Ig do not bind to B7-1 negative cells, which are positive for staining with BB-1 monoclonal antibody. [Boussiotis et al., Proc. Nat'l. Acad. Sci. (USA), 90, 11059 (1993); and Freeman et al., Science, 262, 909 (1993)].

It is concluded that there are at least 3 different B7 molecules, the following table summarizes the binding of B7-24, BB-1 and CTLA-4 IG:

TABLE 7

| Antibody | B7-1 | B7-2 | B7-3 |
|---|---|---|---|
| B7-24 | + | – | – |
| BB-1 | + | – | + |
| CTLA-4Ig | + | + | – |

Alloantigen-specific anergy or tolerance may be induced from the combined use of CsA and B7-24. This induction of tolerance has been demonstrated both for the induction of cytotoxicity by T cells, and for T-cell proliferation (data not shown). This is not obvious, since well cited publications in scientific literature suggest that addition of CsA to T cells prevents the induction of anergy [Jenkins et al., J. Exp. Med., 165, 302 (1987); Jenkins et al., Proc. Nat'l. Acad. Sci. (USA), 54, 5409 (1987); Jenkins et al., J. Immunol., 140, 3324 (1988); Mueller et al., Ann. Rev. Imunol., 7, 445 (1989) and Schwartz, Nature, 248, 1349 (1990)].

Induction of tolerance in an in vivo model of heart transplantation in rats with CTLA-4 Ig is reported only to work when added 2 days after the tissue grafting. Starting the treatment at the same day of the grafting is not reported to result in tolerance. Thus, signaling by B7-2 interaction with T cells is needed for tolerance induction and the blocking effect at day 2 is due to blocking B7-1. With the B7-24 antibody, this is not a problem because in contrast to CTLA-4 Ig, it does not block B7-2. With respect to tolerance induction versus suppression combination of anti-B7-1 with CsA is not obvious signal transduction through the TcR/CD3 complex and anti-B7-2 are needed for tolerance induction. This means that the signals by the TcR/CD3 and B7-2 needed for IL-2 production are sensitive for CsA, but the signal for tolerance induction is not.

Example 15 describes the induction of tolerance using a cell line that expresses both the B7-1 and the B7-2 molecule on the cell surface. Thus it is possible to induce tolerance by blocking B7-1 and CsA, while at the same time the B7-2 molecule is free to interact with CD28 and or CTLA-4 on the T cells. Again this is not suggested in the present literature on the role of the both B7 molecules.

EXAMPLE 15

Cells and Cell Lines

Peripheral blood T cells were isolated from healthy volunteers as described [Van Gool et al., J. Immunol., 150, 3254 (1993)]. The cells were cultured in RPMI 1640 (Gibco, Paisley, Scotland) supplemented with 2mM L-glutamine, penicillin (1000 U/ml), streptomycin (100 µg/ml) and 10% iron-supplemented bovine calf serum (complete medium). Two EBV-transformed B-cell lines were used as stimulator cells for the MLR:ARC, obtained from ATCC, Rockville, Md. (HLA-DR w8,w8) and MM, produced at Innogenetics, Gent, Belgium (HLA-DR 1,2). The P815 cell line obtained from ATCC, Rockville, Md.) is a DBA/2-derived NK-resistant mouse mastocytoma cell line that expresses FCγRII and FcγRIII.

Monoclonal Antibodies and Other Reagents

MAb B7-24 (IgG2a, κ) was obtained from a fusion with splenocytes from a mouse immunized with Sf9 insect cells expressing the human B7 molecule [de Boer et al., Eur. J. Immunol., 22, 3071 (1992) and de Boer et al., J. Immunol. Methods, 152, 15 (1992)] and was used as purified antibody. Anti-CD3 mAb OKT3 (IgG2a, κ) was used as purified antibody isolated from the supernatant of the OKT3-clone obtained from ATCC, Rockville, Md. CsA (purchased from Sandoz Pharmaceuticals, Basel, Switzerland) was dissolved in ethanol (10 mg/ml) and diluted with Phosphate Buffer Saline (pH=7.4) to a stock solution of 8 µg/ml (stored at −20° C.). rIL-2 was obtained through the Biological Response Modifier Program (NCI, Frederick, Md.) and produced by Hoffman-La Roche, or was purchased from Boehringer-Mannheim. rIL-4 was produced at Innogenetics, Gent, Belgium.

Mixed Lymphocyte Reactions (MLR)

For the primary MLR, $10^6$ T cells were cultured with $0.25 \times 10^6$ ARC cells (irradiated with 2000 RAD), for 5 to 7 days in 24-well flat-bottom tissue culture plates in 1 ml medium. MAb B7-24 (10 µg/ml) and/or CsA (400 ng/ml) were added from the beginning of the culture period After 5 to 7 days the cells were harvested, resuspended in medium for analysis of cytotoxic capacity or for further culture in medium alone during 1–2 days the absence of the stimulator cells. The T-cell blasts were restimulated in a secondary MLR with irradiated ARC cells or MM cells at a T cell: :stimulator cell-ratio 4:1 without CsA or anti-B7. Four days later the cells were harvested and resuspended in medium for analysis of cytotoxic capacity or for further culture. If a tertiary MLR was performed, the cells were again restimulated with ARC cells or MM cells (T cell:stimulator cell-ratio 4:1) for 4–5 days without CsA or anti-B7.

Cytotoxicity Assay

Cytotoxic activity as measured in a 4 hour target cell lysis assay using murine P815 cells or ARC cells as targets. In the case of the P815 target cells, the CTL were bridged non-specifically to the target cells using the anti-CD3 mAb OKT3 at 2 µg/ml [Van Gool et al., *J. Immunol.*, 150, 3254 (1993)]. This cytotoxicity assay thus evaluates all T-cell cytotoxic activity, irrespective of antigen-specificity. When the ARC cells were used as target cells, only the alloantigen-specific CTL participate in the killing process. One million target cells were labeled with 200 µCi of $^{51}Cr$ sodium-chromate (Amersham International, Amersham, United Kingdom). The CTL assays were performed in 96-well V-bottom microtiter plates using 5000 $^{51}Cr$-labeled target cells with $5\times10^4$ T cells (E:T ratio=10, unless otherwise indicated) in a total volume of 200 µl/well. Four wells were filled with $5\times10^3$ target cells in 200 µl medium alone, and four wells with $5\times10^3$ target cells in 100 µl medium and 100 µl saponin for evaluation of spontaneous and maximal release, respectively. The percentage anti-CD3-dependent $_{51}Cr$ release of P815 cells was calculated as described [Van Gool et al., *J. Immunol.*, 150, 3254 (1993)]. % lysis of ARC cells was calculated: (Total release by the T cells— Spontaneous release)/(Maximal release by saponin— Spontaneous release)×100.

In FIG. 11 Purified human T cells were stimulated with irradiated ARC cells in a primary (7 d, FIGS.>11A and C, left panels) and a secondary (4 d, FIGS. 11B and D, right panels) MLR. CsA (400 ng/ml) and mAb B7-24 (10 µg/ml) were added during the primary MLR as indicated. CTL activity was measured in an anti-CD3-redirected cytotoxic assay against P815 mastocytoma cells (FIGS. 11A and B, upper panels) and in an alloantigen-specific cytotoxic assay against the original stimulator cells (FIGS. 11C–D lower panels).

The effect of blocking B7 - CD28/CTLA-4 interaction with mAb B7-24, was analyzed in combination with CsA, during a primary MLR of freshly isolated human T cells against EBV-transformed human B-cell line (ARC) on subsequent restimulation with the same cell line. T cells primed with ARC displayed cytotoxic activity after a primary and more so after secondary MLR (FIG. 11). In FIGS. 11A–D, combined data of the cytotoxic activities measured after secondary MLR (n=10, upper panels) or tertiary MLR (n=3, FIGS.>11C and D lower panels) of T cells which were stimulated during a primary MLR, using ARC as stimulator cells, without or with mAb B7-24 (10 µg/ml) and CsA (400 ng/ml). Cytotoxic activity was measured, either in the anti-CD3-redirected cytotoxic assay (left panels), or the alloantigen-specific cytotoxic assay on the original ARC stimulator cells (right panels). The overall cytotoxic activity of the anergic cells was significantly lower compared to the primed cells, measured with the anti-CD3-redirected cytotoxic assay against P815 (t-test of paired samples: p<0.0001) or with an antigen-specific cytotoxic assay against ARC (t-test of paired samples p<0.005).

As demonstrated in FIG. 11, the combination of B7-24 mAb and CsA not each of them separately blocked the generation of CTL during the primary MLR, and, more importantly, inhibited subsequent CTL generation in a secondary MLR performed in the absence of these blocking agents. Tan et al., *J. Exp. Med.*, 177, 165 (1993) demonstrated that CTLA-4-Ig alone induces an alloantigen-specific hyporesponsiveness in human T-cell cultures as measured by proliferation. In our experiments, using a CTL evaluation for anergy induction [Otten et al., *Science*, 251, 1228 (1991) and Go et al., *J. Immunol.*, 150, 367 (1993)], the mAb B7-24 alone did not enter the cells in an anergic state, although we also sometimes found a state of hyporesponsiveness (not shown). However the combination of CsA and mAb B7-24 added during the primary MLR, consistently inhibited alloantigen-induced CTL generation in a secondary MLR (FIG. 12). Varying the CsA concentration from 200 to 1600 ng/ml or the anti-B7 concentration from 0.1 to 10 µg/ml resulted in an identical state of non-responsiveness (not shown). Also after a second restimulation with ARC, the cells made anergic during the primary MLR with CsA and mAb B7-24, displayed no cytotoxic activity (FIG. 12). CsA with anti-CD58 (LFA-3) mAb or with anti-CD54 (ICAM-1) mAb, or mAb B7-24 in combination with mAb against the IL-2 receptor, could not induce this state of non-responsiveness (not shown). To study the alloantigen-specificity of the anergy induction, ARC-primed and unresponsive T cells were restimulated twice with ARC cells (HLA-DR w8,w8) or third party MM (HLA-DR 1,2) cells.

In Table 8, alloantigen-primed or anergic cells were generated depending on whether isolated human T cells were stimulated in the 5 day primary MLR, in the absence (primed cells) or presence (anergic cells) of anti-B7-1 (10 µg/ml) and CsA (400 ng/ml). Following the primary MLR with ARC stimulator cells, and after a 1 day period of culture in medium alone, the cells were restimulated with ARC or with MM (T cell:stimulator cell-ratio 4:1). After five days of secondary MLR, the remaining cells were harvested and cultured in medium alone for 1 day. A tertiary MLR was performed with ARC or MM as indicated (T cell:stimulator cell-ratio 4:1). After the secondary or tertiary MLR the cells were harvested and a cytotoxic assay was performed with an effector:target ratio of 10:1 against anti-CD3-coated P815.

TABLE 8

Allo-antigen specificity of anergy induction * demonstrated by restimulation with the priming cells or third party stimulator cells

| Stimulator cells | | % lysis of P815 cells, by | |
|---|---|---|---|
| Secondary MLR | Tertiary MLR | Primed cells | Anergic cells |
| ARC | — | 40 | 6 |
| MM | — | ND | 38 |
| ARC | ARC | 83 | 8 |
| MM | ARC | ND | 53 |
| ARC | MM | 84 | 16 |
| MM | MM | ND | 54 |

The T cells treated with CsA and B7-24 mAb in a primary MLR towards ARC, displayed cytotoxic activity when restimulated with MM cells, indicating that only the ARC-specific T cells were unresponsive (Table 8). The anergy induction obtained by alloantigen-induced stimulation in the presence of mAb B7-24 and CsA has to be considered as an active process for several reasons. First, a minimum of 5 days culture with stimulator cells, followed by 1 or 2 days culture in medium alone, were needed to yield an anergic state (not shown). The activation marker HLA-DR was expressed on a proportion of the cells (24% and 33% positive cells in two experiments) stimulated with alloantigen in the presence of MAb B7-24 and CsA, compared to 2% and 4% in the starting population and 51% and 31% after stimulation with alloantigen alone. The cells cultured with mAb B7-24 and CsA during alloantigen stimulation did however not express CD25 (IL-2 receptors) and did not switch from the CD45RA (virgin) to the CD45RO (memory) phenotype (not shown). IL-2 has been shown to prevent [Tan et al., *J. Exp. Med.*, 177, 165 (1993)] and to correct [Jenkins et al., *Proc. Nat'l. Acad. Sci.* (USA), 54, 5409 (1987); Mueller et al., *Ann Rev. Immunol.*, 7, 445 (1989) and Schwartz et al., *Cell*, 71, 1065 (1992)] the anergic state of T cells, anergized by antigen stimulation in the absence of costimulatory signals.

Figure 13:
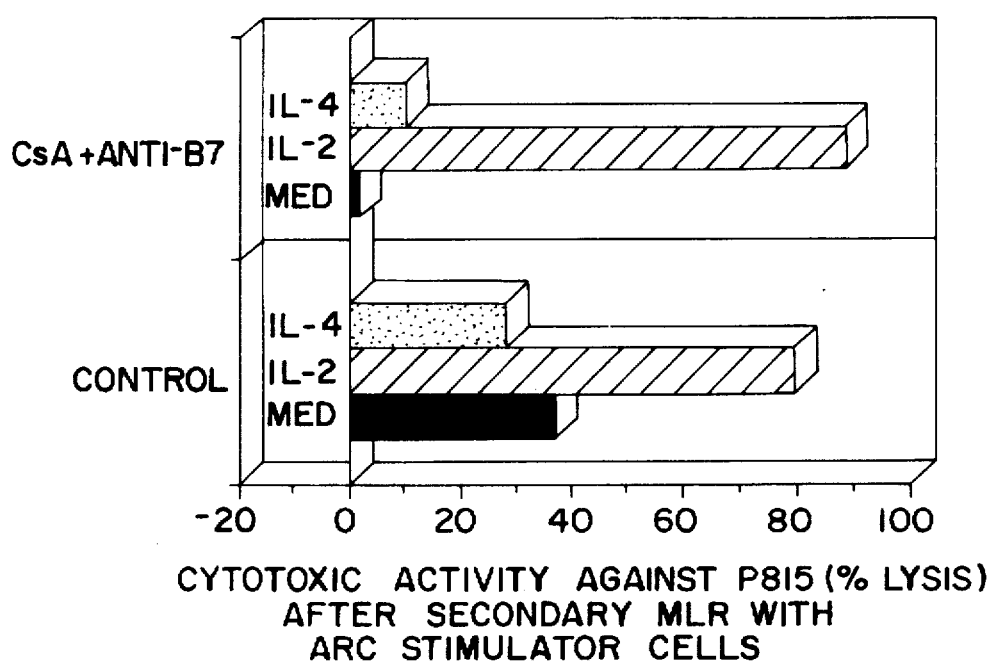
In FIG. 13. bar graphs illustrate that IL-2 prevents the induction of anergy with mAb B7-24 and CsA in a primary MLR.

In FIG. 13 purified human T cells were stimulated with irradiated ARC cells in a primary MLR (5 d) with or without CsA (400 ng/ml) and mAb B7-24 (10 µg/ml). IL-2 (10 U/ml, Hoffman-La Roche) or IL-4 (200 U/ml) were added during the primary MLR as indicated. After the secondary MLR (4 d), CTL activity was measured in an anti-CD3-redirected cytotoxic assay against P815 mastocytoma cells.

FIG. 13 demonstrates that alloantigen-specific anergy-induction in human T cells by CsA and mAb B7-24 could also be prevented by adding IL-2 during the primary MLR. This IL-2 effect may be blocked by mAb anti-Tac and mikβ1 against the p55 and p70 chain of the IL-2 receptor (not shown).

Figure 14A:
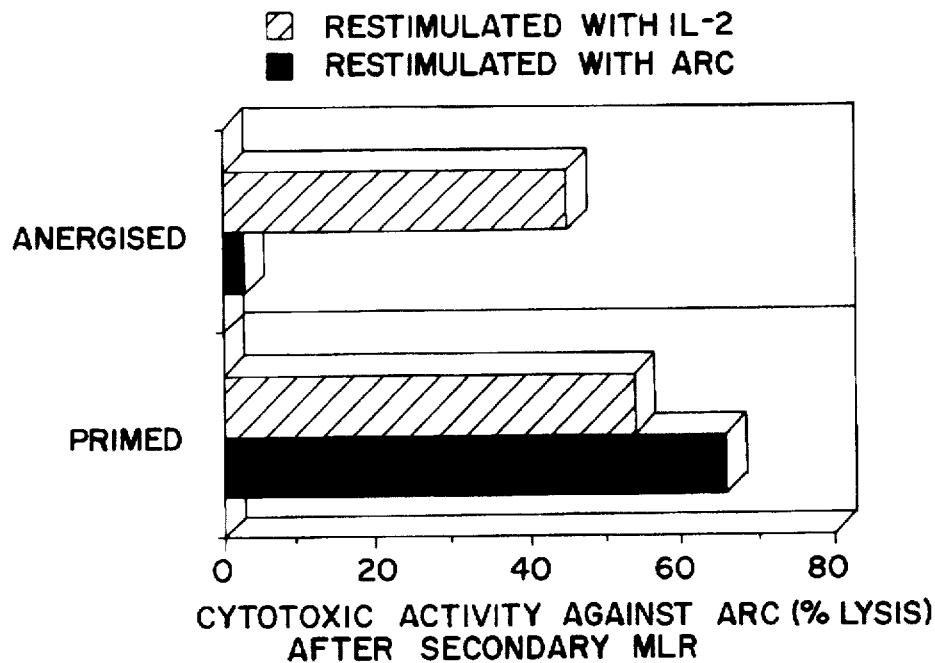
In FIG. 14A–B. bar graphs illustrate that restimulation with IL-2 (FIG. 4A) or with immobilized anti-CD3 (FIG. 4B) reverses anergy.
Figure 14B:
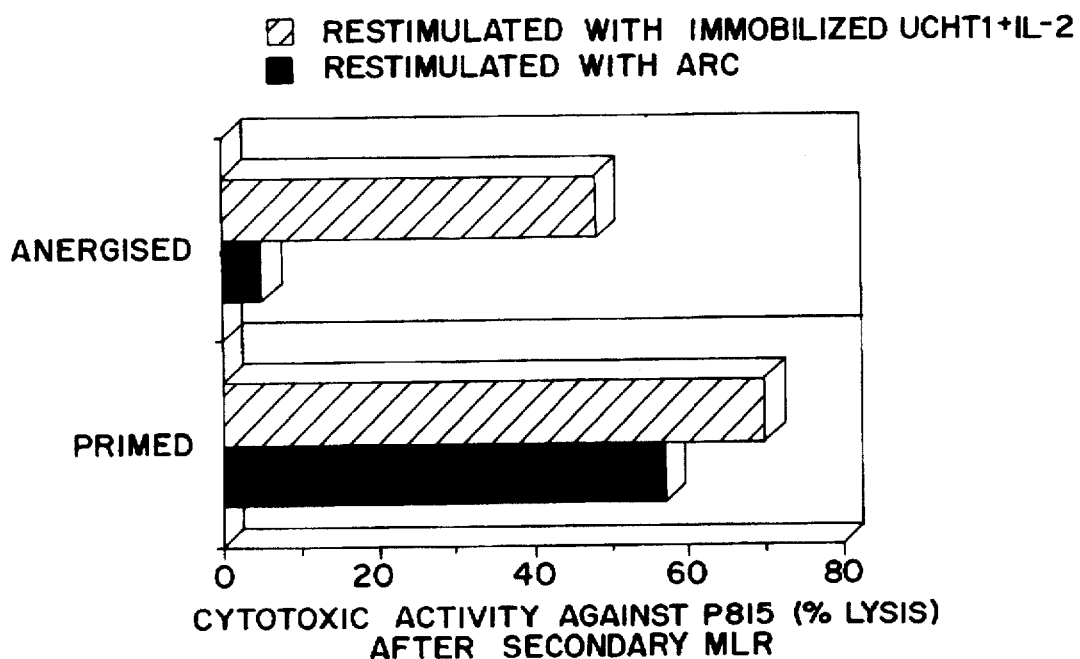

When IL-2 was added during a secondary MLR, the generation of antigen-specific CTL activity in the cultures of anergized cells was strongly restored (FIG. 14A). In FIG. 14A ARC cells or IL-2 (10 U/ml, Boehringer-Mannheim) were added to T cells, primed with RC or anergized against ARC during a primary MLR (7d) with the blocking combination of CsA (400 ng/ml) and mAb B7-24 (10 µg/ml). Antigen-specific CTL activity was measured after 4 days (E:T=20). The data are representative of three experiments. LAK-activity could be excluded. FIG. 14b: primed or anergized T cells were restimulated with ARC cells or with immobilized UCHT1 +IL-2 (10 U/ml, Boehringer-Mannheim) during 4 days. CTL activity was measured in an anti-CD3-redirected cytotoxic assay against P815 mastocytoma cells (E:T=20). The data are representative of two experiments.

Addition of IL-2 during a tertiary MLR could also restore the CTL activity of anergic cells (not shown). When the T cells were rendered anergic, polyclonal cytotoxic activity could be measured after optimal restimulatin with immobilized anti-CD3 mAb UCHT1 and IL-2 (FIG. 14B). These data demonstrate the importance of the IL-2 production defect for induction of the anergic state. It is reported that persistant IL-4 mRNA expression after blocking a MLR with CTLA-4-Ig might be responsible for residual T-cell proliferation in primary or secondary MLR [Tan et al., *J. Exp. Med.*, 177, 165 (1993)]. This might also be responsible for residual CTL generation in the presence of anti-B7-1 alone. However, the data (FIG. 13) do not support this hypothesis because adding IL-4 to the primary MLR in the presence of mAb B7-24 and CsA had no effect.

EXAMPLE 16

Purified peripheral blood lymphocytes ($0.5 \times 10^6$/ml) were cultured with the mitomycin A-treated, alloantigen-expressing EBV-transformed B cell line ARC ($0.12 \times 10^6$/ml) for 6 days in the presence of the additions as noted in the table. After 3 days culture without any additions, the T cells were re-stimulated for 4 days with the ARC cells without further additions. The proliferative response was measured by [$^3$H]-thymidine incorporation. Results are shown in Table 9.

TABLE 9

The combination of CsA and mAb B7-24, but not CsA and CTLA4-Ig can induce alloantigen-specific tolerance

| Additions during Primary MLR | Proliferation of T cells after Secondary MLR (CPM) |
| --- | --- |
| None | 11365 ± 638 |
| Mab B7-24 | 10056 ± 600 |
| CTLA4-Ig | 13969 ± 800 |
| CsA | 12409 ± 547 |
| Mab B7-24 + CsA | 464 ± 166 |
| CTLA4-Ig + CsA | 5004 ± 641 |

Exposure of T cells to alloantigen in a primary MLR results in the priming of alloantigen-specific T cells, which after re-stimulation results in a strong proliferative response. Addition of anti-B7 mAb B7-24, CTLA4-Ig or CsA alone did not influence the proliferative response after secondary stimulation. The combination of mAb B7-24 and CsA during the primary exposure of the T cells with the alloantigen, resulted in alloantigen-specific tolerance, since the T cells could not be re-stimulated with the same alloantigen. In contrast, the combination of CTLA4-Ig and CsA resulted only in a decreased response during the secondary stimulation, but not in alloantigen-specific tolerance.

This experiment provides another example of the differences between mAb B7-24, which only binds to B7-1 and CTLA4-Ig which binds to B7-1 and B7-2. In addition it again demonstrates that blocking both B7-1 and B7-2 does not result in alloantigen-specific tolerance.

The present invention has been described with reference to specific embodiments. However, this application is intended to cover those changes and substitutions which may be made by those skilled in the art without departing from the spirit and the scope of the appended claims.

SEQUENCE LISTING ( 1 ) GENERAL INFORMATION:

( i i i ) NUMBER OF SEQUENCES: 8

( 2 ) INFORMATION FOR SEQ ID NO:1:

( i ) SEQUENCE CHARACTERISTICS:
        ( A ) LENGTH: 27 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:1:

GCGCTGCAGC ATCTGAAGCC ATGGGCC                        27

( 2 ) INFORMATION FOR SEQ ID NO:2:

( i ) SEQUENCE CHARACTERISTICS:
        ( A ) LENGTH: 27 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:2:

CGCGGTACCT TGCTTCTGCG GACACTG                        27

( 2 ) INFORMATION FOR SEQ ID NO:3:

( i ) SEQUENCE CHARACTERISTICS:
        ( A ) LENGTH: 27 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:3:

GCGCTGCAGC ATCTGAAGCC ATGGGCC                        27

( 2 ) INFORMATION FOR SEQ ID NO:4:

( i ) SEQUENCE CHARACTERISTICS:
        ( A ) LENGTH: 61 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:4:

GCGCGGTACC TTACTCCATG GGCATGTATT CCTCTTCCTC GTTATCAGGA AAATGCTGTT    60

G                                                                                                 61

( 2 ) INFORMATION FOR SEQ ID NO:5:

( i ) SEQUENCE CHARACTERISTICS:
        ( A ) LENGTH: 32 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:5:

GCGTAGATCT GGTCTCACCT CGCCATGGTT CG                    32

( 2 ) INFORMATION FOR SEQ ID NO:6:

( i ) SEQUENCE CHARACTERISTICS:

-continued

```
    ( A ) LENGTH: 34 base pairs
    ( B ) TYPE: nucleic acid
    ( C ) STRANDEDNESS: single
    ( D ) TOPOLOGY: linear ( i i ) MOLECULE TYPE: DNA (genomic)

( x i ) SEQUENCE DESCRIPTION: SEQ ID NO:6:

GCGTGGTACC CCACACTCCT GGGTGGGTGC AGCC                               3 4

( 2 ) INFORMATION FOR SEQ ID NO:7:

( i ) SEQUENCE CHARACTERISTICS:
        ( A ) LENGTH: 32 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:7:

GCGTAGATCT GGTCTCACCT CGCCATGGTT CG                                 3 2

( 2 ) INFORMATION FOR SEQ ID NO:8:

( i ) SEQUENCE CHARACTERISTICS:
        ( A ) LENGTH: 61 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:8:

GCGTGGTACC TTACTCCATG GGCATGTATT CCTCTTCCTC ATCAGTCTTG TTTGTGCCTG   6 0

C                                                                   6 1
```

It is claimed:

1. A method for treating transplant rejection in a patient, the method comprising administering to a patient in need of such treatment a therapeutically effective amount of (a) an antibody or an antigen binding fragment thereof that binds to the B7-1 antigen but not to the B7-2 and B7-3 antigens; and (b) an immunosuppressive agent in a pharmaceutically acceptable excipient.

2. A method for treating graft versus host diseases (GVHD) in a patient, the method comprising administering to a patient in need of such treatment a therapeutically effective amount of (a) an antibody or an antigen binding fragment thereof that binds to the B7-1 antigen but not to the B7-2 and B7-3 antigens; and (b) an immunosuppressive agent in a pharmaceutically acceptable excipient.

3. A method for treating rheumatoid arthritis in a patient, the method comprising administering to a patient in need of such treatment a therapeutically effective amount of (a) an antibody or an antigen binding fragment thereof that binds to the B7-1 antigen but not to the B7-2 and B7-3 antigens; and (b) an immunosuppressive agent in a pharmaceutically acceptable excipient.

4. The method of claim 1, 2, 3, wherein the antibody binds to the B7-1 antigen is an anti-B7-1 antibody.

5. The method of claim 1, 2, 3, wherein the immunosuppressive agent is selected from the group consisting of cyclosporin A, FK506, rapamycin and corticosteroids.

6. Monoclonal antibody B7-24 produced by the hybridoma cell line designated ATCC HB11341.

7. The method of claim 4 wherein the anti-B7-1 antibody is a monoclonal antibody.

8. The method of claim 7 wherein the monoclonal antibody is a humanized monoclonal antibody.

9. The method of claim 1, 2, 3, wherein said antibody is an antigen binding fragment of an anti B7-1 antibody that retains the antigen binding function of said antibody.

10. The method of claim 7 wherein the monoclonal antibody is Mab B7-24 produced by the hybridoma cell line designated ATCC HB 11341.

11. The hybridoma cell line ATCC HB 11341 which specifically produces monoclonal antibody B7-24.

12. A composition for inducing T cell anergy comprising in combination:

a) a monoclonal antibody or an antigen binding fragment thereof, said antibody or fragment capable of specifically binding to the B7-1 antigen but not to the B7-2 and B7-3 antigens on the surface of an antigen presenting cell, and b) an immunosuppressive agent; said antibody or fragment and said immunosuppressive agent each being present in an amount that is effective to induce a T cell anergy by the combination that is greater than the sum of the T cell anergies induced by the same amount of each of the components alone.

13. The composition of claim 12 wherein the monoclonal antibody is B7-24 and the antigen binding fragment is a fragment of monoclonal antibody B7-24 produced by the hybridoma cell line designated ATCC HB 11341.

14. The composition of claim 12 wherein the immunosuppressive agent is a member selected from the group consisting of cyclosporin A, FK506, rapamicin and corticosteroids.

15. The composition of claim 12 wherein said monoclonal antibody is a humanized monoclonal antibody.

16. The composition of claim 12 comprising in combination said antigen binding fragment and said immunosuppressive agent.

17. The composition of claim 16 wherein said antigen binding fragment has a humanized component.

* * * * *